US007928292B2

(12) United States Patent
Rommens et al.

(10) Patent No.: US 7,928,292 B2
(45) Date of Patent: Apr. 19, 2011

(54) REFINED PLANT TRANSFORMATION

(75) Inventors: Caius Rommens, Boise, ID (US); J Troy Weeks, Boise, ID (US)

(73) Assignee: J.R. Simplot Company, Boise, ID (US)

( * ) Notice: Subject to any disclaimer, the term of this patent is extended or adjusted under 35 U.S.C. 154(b) by 0 days.

(21) Appl. No.: 12/559,044

(22) Filed: Sep. 14, 2009

(65) Prior Publication Data
US 2010/0199375 A1 Aug. 5, 2010

Related U.S. Application Data

(62) Division of application No. 10/392,301, filed on Mar. 20, 2003, now Pat. No. 7,598,430.

(60) Provisional application No. 60/365,527, filed on Mar. 20, 2002, provisional application No. 60/377,597, filed on May 6, 2002.

(51) Int. Cl.
*C12N 15/84* (2006.01)
*A01H 4/00* (2006.01)
(52) U.S. Cl. ................... 800/294; 800/288; 435/430.1
(58) Field of Classification Search .................. None
See application file for complete search history.

(56) References Cited

U.S. PATENT DOCUMENTS

| | | | |
|---|---|---|---|
| 4,743,548 | A | 5/1988 | Crossway et al. |
| 4,945,050 | A | 7/1990 | Sanford et al. |
| 5,164,310 | A | 11/1992 | Smith et al. |
| 5,284,253 | A | 2/1994 | Watt et al. |
| 5,302,523 | A | 4/1994 | Coffee et al. |
| 5,464,765 | A | 11/1995 | Coffee et al. |
| 5,482,852 | A | 1/1996 | Yodar et al. |
| 5,591,616 | A | 1/1997 | Hiei et al. |
| 5,693,512 | A | 12/1997 | Finer et al. |
| 5,767,373 | A | 6/1998 | Ward et al. |
| 5,959,187 | A | 9/1999 | Bailey et al. |
| 6,018,102 | A | 1/2000 | Garbarino et al. |
| 6,018,106 | A | 1/2000 | Hunt et al. |
| 6,051,757 | A | 4/2000 | Barton et al. |
| 6,054,574 | A | 4/2000 | Quail et al. |
| 6,084,156 | A | 7/2000 | Garbabino et al. |
| 6,132,970 | A | 10/2000 | Stemmer |
| 6,143,949 | A | 11/2000 | Ozawa et al. |
| 6,160,204 | A | 12/2000 | Steffens |
| 6,162,965 | A | 12/2000 | Hansen et al. |
| 6,268,547 | B1 | 7/2001 | Weeks |
| 6,329,567 | B1 | 12/2001 | Jofuku et al. |
| 6,420,547 | B1 | 7/2002 | Maiti et al. |
| 6,448,391 | B1 | 9/2002 | Garbarino et al. |
| 6,660,910 | B1 * | 12/2003 | Damm ........................ 800/300 |
| 6,750,379 | B2 | 6/2004 | McElroy et al. |
| 7,029,908 | B1 * | 4/2006 | Stuiver et al. .............. 435/320.1 |
| 7,057,090 | B1 | 6/2006 | Zilinskas et al. |
| 7,265,267 | B1 * | 9/2007 | De Veylder et al. .......... 800/290 |
| 2001/0026939 | A1 | 10/2001 | Rice et al. |
| 2002/0046415 | A1 | 4/2002 | Albert et al. |
| 2003/0135891 | A1 | 7/2003 | Gould et al. |
| 2006/0212973 | A1 | 9/2006 | Zilinskas et al. |

FOREIGN PATENT DOCUMENTS

| | | |
|---|---|---|
| CA | 1340925 | 5/1987 |
| EP | 0 672 752 A1 | 9/1995 |
| EP | 1 198 985 A1 | 4/2002 |
| WO | WO 98/49332 | 11/1998 |
| WO | WO 98/56932 | 12/1998 |
| WO | WO 99/38979 A1 | 8/1999 |
| WO | WO 00/56906 A | 9/2000 |
| WO | WO 01/25455 A | 4/2001 |
| WO | WO 01/44482 | 6/2001 |
| WO | WO 01/94394 A2 | 12/2001 |
| WO | WO 02/36786 A | 5/2002 |
| WO | WO 02/102979 A2 | 12/2002 |
| WO | WO 03/079765 A2 | 10/2003 |
| WO | WO 2004/007694 A2 | 1/2004 |

OTHER PUBLICATIONS

Nikam et al. Plant Cell, Tissue and Organ Culture 55(1): 15-22 (Oct. 1999).*
Gould et al., "Adaptation of Cotton Shoot Apex Culture to *Agrobacterium*-Mediated Transformation", 1998, vol. 16, pp. 1-10, *Plant Molecular Biology Reporter*.
Fisscher, et al., "Identification of Potential Regulatory Elements in the Far-Upstream Region of the Arabidopsis Thaliana Plastocyanin Promoter," 1994, vol. 26, pp. 873-886, *Plant Molecular Biology*.
Pwee, et al., "The Pea Plastocyanin Promoter Directs Cell-Specific But Not Full Light-Regulated Expression in Transgenic Tobacco Plants,"1993, vol. 3 No. 3, pp. 437-449, *The Plant Journal*.
Cheng, V-H, et al., "Efficient Transformation of Papaya by Coat Protein Agrobacterium Following Liquid-Phase Wounding of Embryogenic Tissues with Carborundum", *Plant Cell Reports*, Springer Verlag, DE., vol. 16, No. 3-4, 1996, pp. 127-132.
De Buck et al., "T-DNA vector backbone sequences are frequently integrated into the genome of transgenic plants obtained by Agrobacterium-mediated transformation", *Mol. Breeding*, vol. 6, No. 5, Oct. 2000, pp. 459-468.
Hanson et al, "Simple Method to Enrich an Agrobacterium-Transformed Population for Plants Containing Only T-DNA Sequences", *Plant Journal*, vol. 19, No. 6, Blackwell Scientific Publications, Oxford, GB, 1999, pp. 727-734.
Rohini et al, Embryo transformation, a practical approach for realizing transgenic plants of safflower , *Annals of Botany* (London), vol. 86, No. 5, Nov. 2000, pp. 1043-1049.
Weeks et al., "Wheat transformation using cyanamide as a new selective agent"; *Crop Science*, vol. 40, No. 6, Nov. 2000, pp. 1749-1754.
Maier-Greiner et al., "Isolation and properties of a nitrite hydratase from the soil fungus *Myrothecium verrucarla* that is highly specific for the fertilizer cyanamide and cloning of its gene," Proc. Natl. Acad. Sci., USA, May 1991, vol. 88, pp. 4260-4264.
Bailey and Gribskov, "Combining evidence using p-values: application to sequence homology searches," *Bioinformatics*, vol. 14, pp. 48-54 (1998).

(Continued)

Primary Examiner — David T Fox
(74) Attorney, Agent, or Firm — Foley & Lardner LLP

(57) ABSTRACT

The present invention provides methods for producing transgenic plants based on an optimized transfer of DNA from *Agrobacterium* to plant cells, and/or on an optimized integration of the transferred DNAs into plant cell genomes. It also provides *Agrobacterium*-transformation vectors that can be used to limit or eliminate the transfer of undesirable DNA. The present invention can be applied to essentially any species of plants, including many recalcitrant plant species.

4 Claims, 3 Drawing Sheets

OTHER PUBLICATIONS

Bechtold et al., "In planta Agrobacterium mediated gene transfer by infiltration of adult Arabidopsis thaliana plants," *Acad Sci Paris Life Sci.*, vol. 316, pp. 1194-1199 (1993).

Clough & Bent, "Floral dip: a simplified method for Agrobacterium-mediated transformation of Arabidopsis thaliana," *The Plant Journal*, vol. 16, pp. 735-743 (1998).

Coca et al., "Differential regulation of small heat-shock genes in plants: analysis of a water-stress-inducible and developmentally activated sunflower promoter," *Plant Molecular Biology*, vol. 31, pp. 863-876 (1996).

De Buck et al., "Agrobacterium tumefaciens Transformation and Cotransforrnation Frequencies of Arabidopsis thaliana Root Explants and Tobacco Protoplasts," *Mol. Plant Microbe Interact.*, vol. 11, pp. 449-457 (1998).

De Neve et al., "T-DNA integration patterns in co-transformed plant cells suggest that T-DNA repeats originate from co-integration of separate T-DNAs," *The Plant Journal*, vol. 11, pp. 15-29 (1997).

During, "A plant transformation vector with a minimal T-DNA," *Transgenic Research*, vol. 3, pp. 138-140 (1994).

Jefferson et al., "GUS fusions: β-glucuronidase as a sensitive and versatile gene fusion marker in higher plants," *The EMBO Journal*, vol. 6, pp. 3901-3907 (1987).

Kononov et al., "Integration of T-DNA binary vector 'backbone' sequences into the tobacco genome: evidence for multiple complex patterns of integration," *The Plant Journal*, vol. 11, No. 5, pp. 945-957 (1997).

Lee et al., "The Arabidopsis HOS1 gene negatively regulates cold signal transduction and encodes a Ring finger protein that displays cold-regulated nucleo-cytoplasmic partitioning," *Gene and Development*, vol. 15, pp. 912-924 (2001).

Murashige & Skoog, "A Revised Medium for Rapid Growth and Bio Assays with Tobacco Tissue Cultures," *Physiol. Plant*, vol. 15, pp. 473-479 (1962).

Mysore et al., "Role of the Agrobacterium tumefaciens VirD2 Protein in T-DNA Transfer and Integration," *Mol. Plant Microbe Interact.*, vol. 11, No. 7, pp. 668-683 (1998).

Shurvinton et al., "A nuclear localization signal and the C-terminal omega sequence in the Agrobacterium tumefaciens VirD2 endonuclease are important for tumor formation," *Proc. Natl. Acad. Sci. U.S.A.*, vol. 89, pp. 11837-11841 (1992).

The Food and Agriculture Organization of the United Nations' Agricultural Services Bulletin No. 108, entitled, "Plant Tissue Culture: An Alternative for Production of Useful Metabolite" by Masanaru Misawa of Bio International Inc., Toronto, Canada http://www.fao.org/docrep/t0831e/t0831e00.htm#con, (1994).

Van Haaren et al., "Mutational analysis of the conserved domains of a T-region border repeat of Agrobacterium tumefaciens," *Plant Molecular Biology*, vol. 13, pp. 523-531 (1989).

Waters et al., "Sequence identity in the nick regions of IncP plasmid transfer origins and T-DNA borders of Agrobacterium Ti plasmids," *Proc Natl Acad Sci.*, vol. 88, pp. 1456-1460 (1991).

Weigel et al., "Activation Tagging in Arabidopsiss," *Plant Physiology*, vol. 122, pp. 1003-1013 (2000).

Trieu et al., "Transformation of Medicago truncatula via infiltration of seedlings or flowering plants with Agrobacterium." *Plant Journal*, Jun. 22, 2000, vol. 6, pp. 531-541, (2000).

Feldmann et al. Molecular and General Genetics 208:1-9 (1987).

Kumar et al., Trends in Plant Science 6(4): pp. 155-159, Apr. 2001.

Swoboda et al., The EMBO Journal 13(2): pp. 484-489, (1994).

Muller-Rober, "One of two different ADP-glucose pyrophosphorylase genes from genes from potato responds strongly to elevated levels of sucrose." *Molecular and General Genetics*, 224:136-146.

Bertagne-Sagnard et al., "Selection of transgenic flax plants is facilitated by spectinomycin." *Transgenic Research*, 5:131-137.

Salomon & Puchta, "Capture of genomic and T-DNA sequences during double-strand break repair in somatic plant cells," *The EMBO Journal*, (1998) 17, 6086-6095.

Trick, *Transgenic Research*, 6:329-336, (1997).

Jackson, "Sensing and repairing DNA double-strand breaks." *Carcinogenesis*, 23: 667-696 (2002).

Puchta, "Induction of intrachromosomomal homologous recombination in whole plants." *The Plant Journal*, 7:203-210, (1995).

Weeks et al., "Wheat Transformation using Cyanamide as a New Selective Agent," *Crop Science*, 40:1749-1754 (2000).

Charity et al., *Plant Cell Tissue Culture and Organ Culture*, 70:51-60, (2002).

Zuker et al., Wounding by bombardment yields highly efficient Agrobacterium-mediated transformation of carnation (Dianthus caryophyllus L.) 5:367-375 (1999).

Cheng et al., *Plant Cell Reports*, 16:127-132 (1996).

\* cited by examiner

Figure 2

**Alignment of the *CAH* gene from *Myrothecium verrucaria* with a new cyanamide tolerance gene isolated from *Aspergillus* (CAH-H1) and a non-functional yeast *CAH* homolog (CAH-H2)**

```
CAH             MSSSEVKANGWTAVPVSAKAIVDSLGKLGDVSSYSVEDIAFPAADKLVAEAQAFVKARLS 60
CAH-H1          MCQNEVEVNGWTSMPADAGAIFDGGPFINVPEALSIEEIKFPVDDPIVEKTMRYAKAALP 60
CAH-H2          -----MSQYGFVRVPREVEKAIP------VVNAPRPRAVVPPPNSETARLVREYAAKELT 49
                     :.  *:. :* ..   .         .:   . :  *  .  .  .  :.   *.

CAH             PETYNHSMRVFYW------------------GTVIARRLLPEQAKDLSPSTWALTCLLHD 102
CAH-H1          TETFNHSMRVYYYGMQDCASHGVLINRSQALGMAITKQQFPKQASALSPSTWALTCLLHD 120
CAH-H2          APVLNHSLRVFQY------------------SVAIIRDQFP--AWDLDQEVLYVTCLLHD 89
                . . ***:**: :                  . .* :  :*  *  *. ..  :******

CAH             VGTAEAYFTSTRMSFDIYGGIKAMEVLK-VLGSSTDQAEAVAEAIIRHEDVGVDGNITFL 161
CAH-H1          IGTSDHNLAATRMSFDIYGGIKALEVLK-GFGATSDQAEAVAEAIIRHQDLGVHGTITYI 179
CAH-H2          IATTDKNMRATKMSFEYYGGILSRELVFNATGGNQDYADAVTEAIIRHQDLTGTGYITTL 149
                :.*::  : :*:***: **** : *::    *.. * *:**:******:*:   * ** :

CAH             GQLIQLATLYDNVGAYDGIDDFGSWVDDTTRNSINTAFPRHGWCSWFACTVRKEESNKPW 221
CAH-H1          GQLIQLATIYDNVGAHPYVKDFGELIHDTTRSQVHEAHPPGEWRTFFSGVIQKEQAIKPW 239
CAH-H2          GLILQIATTLDNVGSN------TDLIHIDTVSAINEQFPRLHWLSCFATVVDTENSRKPW 203
                * ::*:**  ****:        . :.  * . ::  .*   * : *: .: .*:: ***

CAH             CHTTHIPQ-FDKQMEANTLMKPWE 244
CAH-H1          CHTKKMVN-VLRKGSRHPDGQ--- 259
CAH-H2          GHTSSLGDDFSKKVICNTFGYN-- 225
                 **. : : . ::   :.
```

Figure 3

Alignment between a new ubiquitin-like promoter (UbiN) and the corresponding part of the sugarcane Ubiquitin-4 promoter.

```
Ubi4    AAGCAAACGGTATAGCAACGGTGTTAACCTGATCTAGTGATCTCTTGCAATCCTTAACGG 60
UbiN    AAGCAAAGGGTATGGCAACTGTGTCACCGCCCTTCGCTG----CGTG------TTAACGG 50
        ******* **** **** **** * *    *    **     * **       ******

Ubi4    CCACCTACCGCAGGTAGCAAACGGCGTCCCCCTCCTCGATATCTCCGCGGCGACCTCTGG 120
UbiN    CCACCAACCGCAGGTAGCAAACGGCGTGCACCTTCCCGAGATCTCCACAGCGAGGTCTGG 110
        ***** ********************* *** * *** ****** * ****  *****

Ubi4    CTTTTTCCGCGGAATTGCGCGGTGGGGACGGATTCCACAACCGCGACGCAA-CCGCCTCT 179
UbiN    CTTTTTCCGCCTTCCCG-GAAACCGCGGTGGTTTC----AGCGTGGCGGATTCCCCCTCC 165
        **********    * *       * ** ***    * ** * **   ** ****

Ubi4    CGCCGCTGGGCCCCACACCGCTCGGTGCCGTAGCCTCACGGGACTCTTTCTCCCTCCTCC 239
UbiN    CACCACCCAACCGC-CATAAATACCAGCCCCCACCTCACT---CTCTTTGCATATCCATC 221
        * ** *   **  *  *   *   ******      ******    *** *

Ubi4    CCCGTTATAAATTGGCTTCATCCCCTCCTTGCCTC 274
UbiN    CAAATCCCA----GTCCCCAATC------------ 240
        *    *  *     * *   **  *
```

REFINED PLANT TRANSFORMATION

CROSS-REFERENCE TO RELATED PATENT APPLICATIONS

This Non-Provisional application is a divisional application of Non-Provisional Ser. No. 10/392,301, filed on Mar. 20, 2003, now U.S. Pat. No. 7,598,430, which claims priority to U.S. Applications 60/365,527, filed Mar. 20, 2002, and 60/377,597, filed May 6, 2002, each of which is incorporated herein by reference in their entirety.

BACKGROUND OF THE INVENTION

The ability to transform plants by integrating and expressing desirable polynucleotides in plant cells makes it possible to efficiently introduce agronomic and quality traits into a variety of plant species. Transgenic plants that are produced by current transformation methods, however, require extensive tissue culture manipulations, which are time consuming and species specific. Furthermore, such methods do not only integrate the desirable polynucleotide(s) into a plant's genome, but also additional and superfluous nucleic acids. When making a genetically engineered food, the superfluous nucleic acids may be undesirable because they are from non-food sources, such as viruses and bacteria and are, therefore, undesirable.

Existing plant transformation methods rely on the use of *Agrobacterium* for DNA transfer. These methods typically comprise (1) preparing tissue explants, (2) infecting explants with at least one disarmed *Agrobacterium* strain, (3) culturing and selecting the transformed plant cells on tissue culture media, and (4) inducing proliferation and subsequent regeneration to generate whole plants. Examples of these methods are described in U.S. Pat. Nos. 5,591,616, 6,051,757, 5,164,310, and 5,693,512, and EP 0 672 752 A1, which are incorporated herein by reference. However, explant preparation is a laborious process that requires extensive resources, especially for many monocotyledonous plant species including maize, wheat, barley, and oats.

Furthermore, the subsequent process of proliferation and regeneration is also very laborious, taking at least 12 months to develop a primary transformed plant. Since different plants require different concentrations of salts, minerals, and hormones, including auxins and cytokinins, for proliferation and regeneration, the applicability of typical transformation methods is limited to one species or only a few cultivars of one species.

Even by optimizing cultivar-specific transformation methods, successful transformation has been accomplished for only a very few cultivars of important crop species, such as for the maize inbred lines H99, Oh43, and B73, the spring wheat variety Bobwhite, and the cotton cultivar Coker 312. The introduction of foreign DNA into elite germplasm often requires the transformation of inferior cultivars followed by conventional multi-year breeding programs to introgress the DNA into the desired material.

Tissue culture manipulations can be avoided by either vacuum infiltrating plants with an *Agrobacterium* suspension or emerging such plants in suspensions that also contain approximately 0.05% Silwet L-77 (Bechtold et al., *Acad Sci Paris Life Sci* 316: 1194-1199, 1993; Clough & Bent, *Plant J* 16: 735-743, 1998). However, this method is only applicable to the model plant systems *Arabidopsis thaliana*, *Arabidopsis lasiocarpa*, and *Raphanus sativus*. Transgenic plants can also be obtained for a fourth plant species, *Medicago trunculata*, by vacuum infiltrating seedling with *Agrobacterium* suspensions.

Such in planta transformation systems are of limited utility, however, and not applicable to commercially relevant crop plants. Efforts to broaden such applicability to encompass a larger variety of crops have failed because of the inaccessibility of those crops to *Agrobacterium*-mediated transformation, and/or the resultant, detrimental physiological responses, such as flower abscission and *Agrobacterium*-induced necrosis.

Alternative transformation systems include direct DNA delivery systems like particle bombardment (U.S. Pat. No. 4,945,050), polyethylene glycol treatment (U.S. Pat. No. 6,143,949), microinjection (U.S. Pat. No. 4,743,548), whiskers (U.S. Pat. No. 5,302,523), and electroporation (U.S. Pat. No. 5,284,253). Whereas DNA transfer mediated by *Agrobacterium* is often limited to one to three copies of foreign DNA, direct DNA delivery systems usually result in the transfer of many more copies, which may integrate randomly throughout the plant genome. The unnecessary abundance of insertions is undesirable and may negatively affect the plant genome's integrity.

Sonication was shown to greatly enhance the efficiency of both *Agrobacterium*-mediated transformation and direct DNA delivery (U.S. Pat. No. 5,693,512). The ultrasound vibrations are believed to disrupt cell walls and thereby facilitate foreign DNA transfer. Sonication reduces the viability of tissue explants, and any increase in transformation frequency may be compromised by an increase in non-viable or dying plants.

These, as well as more conventional transformation methods, introduce a variety of viral and bacterial genetic elements into plant cells. At least four different genetic elements, derived from bacteria, are typically used to transform plants (During, *Transgenic Research* 3: 138-40, 1994). Such elements include regulatory sequences such as promoters and terminators to promote appropriate transgene expression in plants. An example of a frequently used foreign promoter is the 35S "super" promoter of Cauliflower Mosaic Virus (CaMV), which is able to not only induce high levels of expression of the transgenes but also enhance the expression of native genes in its vicinity (Weigel et al., *Plant Physiol.*, 122: 1003-13, 2000).

Other strong viral promoters include those from rice tungro bacilliform virus, maize streak virus, cassava vein virus, mirabilis virus, peanut chlorotic streak caulimovirus, figwort mosaic virus and *chlorella* virus. Other frequently used promoters are derived from bacterial species and include the promoters of the nopaline synthase and octopine synthase gene. Only a few strong and constitutive promoters are derived from food sources. Examples of such promoters are the promoters of the maize Ubiquitin-1 gene (U.S. Pat. No. 6,054,574; and WO 01/94394), the sugarcane Ubiquitin-4 gene (U.S. Patent application 02/0046415), and the potato Ubiquitin-7 gene (Garbarino et al., U.S. Pat. No. 6,448,391 B1, 2002). The applicability of most other plant promoters is limited because of low activity, tissue specificity, and/or poor developmental regulation. Typical terminators are those associated with the nopaline synthase and octopine synthase genes from *Agrobacterium*.

Also required for transformation is the *Agrobacterium*-derived transfer DNA, i.e., the T-DNA, which transfers desired polynucleotide(s) from *Agrobacterium* into plant cell genomes. Thus, transgenic plants of the conventional art contain much superfluous foreign DNA. Furthermore, the infidelity of DNA transfer can result in co-integration of bacterial plasmid sequences that are adjacent to the T-DNA. In fact, about 75% of transformation events in plants such as tomato, tobacco, and potato may contain such superfluous plasmid backbone DNA (Kononov et al., *Plant J.* 11: 945-57, 1997). The presence of backbone sequences is undesirable because they contain bacterial origins of replication and/or encode for antibiotic resistance genes.

Thus, there is a need for accelerated and species-independent methods for transferring and expressing desired polynucleotides into plant cells and genomes. There is also a need to limit the co-transfer of superfluous, undesirable DNA, if the target plant is a food crop. Such methods are provided herein. To optimize DNA transfer from *Agrobacterium* to individual plant cell nuclei, plant tissues such as seedlings are agitated in an *Agrobacterium* suspension. To optimize the subsequent integration of the transferred DNAs into the genome of plant cell nuclei, the plant tissues are exposed to chemicals that induce double strand breaks. Vectors are used that are designed to limit the transfer of undesirable DNA.

SUMMARY OF THE INVENTION

According to the present invention, a method ("method 1") for producing a transgenic plant is provided. The method comprises (a) agitating a solution comprising a germinating plant seedling, or explant thereof, and at least one *Agrobacterium* strain that harbors a plasmid vector carrying a desired polynucleotide; (b) cultivating the seedling to produce a plant; and (c) screening the plant to determine if the desired polynucleotide is integrated into the genome of at least one cell of the plant, wherein the plant is stably transformed, and wherein the step of agitating the solution does not comprise sonication.

In one preferred embodiment the germinating plant seedling is from a monocotyledenous plant. In another embodiment, the monocotyledenous plant is selected from the group consisting of turfgrass, wheat, maize, rice, oat, barley, orchid, iris, lily, onion, and sorghum. In another embodiment, the turfgrass is selected from the group consisting of *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra* commutata (fine fescue), *Cynodon dactylon* (common bermudagrass); *Pennisetum clandestinum* (kikuyugrass), *Stenotaphrum secundatum* (st. augustinegrass), *Zoysia japonica* (zoysiagrass), and *Dichondra micrantha*.

In another preferred embodiment, the germinating plant seedling is from a dicotyledenous plant. In one embodiment, the dicotyledenous plant is selected from the group consisting of cotton, tobacco, *Arabidopsis*, tomato, potato, sugar beet, broccoli, cassava, sweet potato, pepper, poinsettia, legumes, alfalfa, soybean, carrot, strawberry, lettuce, oak, maple, walnut, rose, mint, squash, daisy, geranium, and cactus.

In another embodiment, the expression of the desired polynucleotide in the stably transformed plant confers a trait to the plant selected from the group consisting of increased drought tolerance, reduced height, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved taste, improved texture, decreased phosphate content, increased germination, increased micronutrient uptake, improved starch composition, improved flower longevity, and production of novel proteins or peptides.

In a preferred embodiment, the desired polynucleotide of the present invention is selected from the group consisting of a gene or part thereof, the 5'-untranslated region of the gene, the 3'-untranslated region of the gene, the leader sequence associated with the gene, or the trailer sequence associated with the gene.

In a preferred embodiment, the gene encodes a protein that is selected from the group consisting of an antifungal, a nutritional peptide or protein, a transcription factor, a receptor that binds to pathogen-derived ligands, a hemoglobin, an oxidase, an enzyme of the lignin biosynthesis pathway, an enzyme of industrial value, or an antigen. Preferably, the desired polynucleotide is operably linked to a promoter and a terminator.

In a preferred embodiment, the sequences of the promoter and the terminator naturally occur in the genome of plants, or are isolated from human food sources.

According to the method, the vector comprises (a) a T-DNA or a P-DNA that comprises (i) the desired polynucleotide, and (ii) a selectable marker gene operably linked to a terminator that is not naturally expressed in plants; and (b) a backbone integration marker gene, wherein the desired polynucleotide and the selectable marker gene are positioned between the border sequences of the T-DNA or between the border-like sequences of the P-DNA, and wherein the backbone integration marker gene is not positioned within the T-DNA or within the P-DNA.

In one embodiment, the desired polynucleotide in the vector is operably linked to a promoter and a terminator.

In another embodiment, the backbone integration marker gene is operably linked to a promoter and a terminator. In one embodiment, the backbone integration marker is a cytokinin gene. In yet another embodiment, the cytokinin gene is IPT, and the plant is a dicotyledon plant. In another embodiment, the backbone integration marker is PGA22, TZS, HOC1, CKI1, or ESR1.

In yet another embodiment, the border-like sequences of the P-DNA range in size from 20 to 100 by and share between 52% and 96% sequence identity with a T-DNA border sequence from *Agrobacterium tumafaciens*.

In another embodiment, expression of the selectable marker gene confers fertilizer tolerance to the transgenic plant and progeny thereof.

In another embodiment, the selectable marker gene that confers fertilizer tolerance is a selectable marker gene that confers resistance to cyanamide.

In another embodiment, the selectable marker gene that confers resistance to cyanamide is selected from the group consisting of CAH and CAH homologs derived from certain cyanamide tolerant soil fungi including *Aspergillus, Penicillium*, and *Cladosporium*. In another embodiment, the selectable marker gene is operably linked to a yeast ADH terminator. In another embodiment, the selectable marker gene is an antibiotic resistance gene. In yet another embodiment, the antibiotic resistance gene is selected from the group of genes encoding hygromycin phosphotransferase, neomycin phosphotransferase, streptomycin phosphotransferase, and bleomycin-binding protein. In another embodiment, the selectable marker gene is a herbicide resistance gene. In another embodiment, the herbicide resistance gene is selected from the group of genes encoding 5-enolpyruvylshikimate-3-phosphate synthase, glyphosate oxidoreductase, glyphosate-N-acetyltransferase, and phosphinothricin acetyl transferase.

In a preferred embodiment, the step of agitating the solution is accomplished by vortexing. In another embodiment, the solution is vortexed from about 60 seconds to several hours. In yet another embodiment, the solution is vortexed for about 5 minutes to about 30 minutes.

In one other embodiment, the step of cultivating the seedling to produce a transgenic plant comprises transferring the *Agrobacterium*-transformed seedling to soil, and exposing the transformed seedling to conditions that promote growth.

In another embodiment, the step of cultivating the seedling to produce transgenic plants comprises cultivating the *Agrobacterium*-transformed seedling in or on tissue culture medium prior to transferring the transformed seedling to soil, and exposing the transformed seedling to conditions that promote growth.

The method further comprises (i) producing a callus from the transformed seedling cultivated on tissue culture medium; and (ii) inducing shoot and root formation from the callus, prior to transferring to soil. In this case, the transformation vector may comprises (a) a T-DNA or a P-DNA that comprises (i) the desired polynucleotide, and (ii) a selectable marker gene operably linked to a terminator that is not naturally expressed in plants; and (b) a backbone integration marker gene, wherein the desired polynucleotide and the selectable marker gene are positioned between the border sequences of the T-DNA or between the border-like sequences of the P-DNA, and wherein the backbone integration marker gene is not positioned within the T-DNA or within the P-DNA.

Furthermore, in one embodiment, the step of producing a callus from the transformed seedling comprises (i) transferring the transformed seedling to tissue culture media that contains auxin and cyanamide; (ii) selecting fertilizer-tolerant calli; (iii) inducing shoot and root formation from the calli; and (iv) transferring calli with shoots and roots to soil and exposing the calli to conditions that promote growth of the transgenic plants from the calli.

According to method 1, the transformed plant seedling is grown to maturity, crossed to a non-transformed plant and the desired polynucleotide transmitted to at least one progeny plant.

In another embodiment, the transformed plant seedling is grown to maturity, selfed, and the desired polynucleotide transmitted to progeny.

In another aspect of the invention a transformation vector is provided. In one embodiment, the vector can be maintained in *Agrobacterium*, and comprises: (a) a T-DNA or a P-DNA that comprises (i) a desired polynucleotide, and (ii) a selectable marker gene that is operably linked to a terminator not naturally expressed in plants, and (b) a backbone integration marker gene, wherein the desired polynucleotide and the selectable marker gene are positioned between the border sequences of the T-DNA or between the border-like sequences of the P-DNA, and wherein the backbone integration marker gene is not positioned within the T-DNA or within the P-DNA. In another embodiment, the desired polynucleotide is operably linked to a promoter and a terminator.

In another preferred embodiment, the backbone integration marker gene is operably linked to a promoter and a terminator.

In another embodiment, the backbone integration marker gene is operably linked to a promoter and a terminator. In one embodiment, the backbone integration marker is a cytokinin gene. In yet another embodiment, the cytokinin gene is IPT, and the plant is a dicotyledon plant. In another embodiment, the backbone integration marker is PGA22, TZS, HOC1, CKI1, or ESR1.

In yet another embodiment, the border-like sequences of the P-DNA range in size from 20 to 100 by and share between 52% and 96% sequence identity with a T-DNA border sequence from *Agrobacterium tumafaciens*.

In another embodiment, expression of the selectable marker gene confers fertilizer tolerance to the transgenic plant and progeny thereof.

In another embodiment, the selectable marker gene that confers fertilizer tolerance is a selectable marker gene that confers resistance to cyanamide.

In another embodiment, the selectable marker gene that confers resistance to cyanamide is selected from the group consisting of CAH or CAH homologs derived from certain cyanamide tolerant soil fungi including *Aspergillus, Penicillium*, and *Cladosporium*. In another embodiment, the selectable marker gene is operably linked to a yeast ADH terminator. In another embodiment, the selectable marker gene is an antibiotic resistance gene. In yet another embodiment, the antibiotic resistance gene is selected from the group of genes encoding hygromycin phosphotransferase, neomycin phosphotransferase, streptomycin phosphotransferase, and bleomycin-binding protein. In another embodiment, the selectable marker gene is a herbicide resistance gene. In another embodiment, the herbicide resistance gene is selected from the group of genes encoding 5-enolpyruvylshikimate-3-phosphate synthase, glyphosate oxidoreductase, glyphosate-N-acetyltransferase, and phosphinothricin acetyl transferase.

In another embodiment, the promoter and the terminator naturally occur in plants. In another embodiment, the desired polynucleotide comprises a gene derived from an edible food source.

In one embodiment, expression of the desired polynucleotide in the transformation vector confers a trait to plants that comprise the desired polynucleotide in their genomes, wherein the trait is selected from the group consisting of increased drought tolerance, reduced height, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved taste, improved texture, decreased phosphate content, increased germination, increased micronutrient uptake, improved starch composition, and improved flower longevity.

In another aspect of the present invention, a method ("method 2") for producing a transgenic plant, comprising: (A) infecting plant tissue with an *Agrobacterium* transformation vector that comprises (i) a T-DNA or a P-DNA that comprises (a) the desired polynucleotide, and (b) a selectable marker gene operably linked to a terminator that is not naturally expressed in plants; and (ii) a backbone integration marker gene, wherein the desired polynucleotide and the selectable marker gene are positioned between the border sequences of the T-DNA or between the border-like sequences of the P-DNA, and wherein the backbone integration marker gene is not positioned within the T-DNA or within the P-DNA; (B) cultivating the seedling to produce plants; and (C) screening the plants for stable integration of the desired polynucleotide.

In one embodiment, the plant tissue is a germinating plant seedling. In another embodiment, the desired polynucleotide is operably linked to a promoter and a terminator. In another embodiment, the backbone integration marker gene is operably linked to a promoter and a terminator. In one embodiment, the backbone integration marker is a cytokinin gene. In yet another embodiment, the cytokinin gene is IPT, and the plant is a dicotyledon plant. In another embodiment, the backbone integration marker is PGA22, TZS, HOC1, CKI1, or ESR1.

In yet another embodiment, the border-like sequences of the P-DNA range in size from 20 to 100 by and share between 52% and 96% sequence identity with a T-DNA border sequence from *Agrobacterium tumafaciens*.

In another embodiment, expression of the selectable marker gene confers fertilizer tolerance to the transgenic plant and progeny thereof.

In another embodiment, the selectable marker gene that confers fertilizer tolerance is a selectable marker gene that confers resistance to cyanamide.

In another embodiment, the selectable marker gene that confers resistance to cyanamide is selected from the group consisting of CAH and functional CAH homologs. In another embodiment, the selectable marker gene is operably linked to a yeast ADH terminator. In another embodiment, the selectable marker gene is an antibiotic resistance gene. In yet another embodiment, the antibiotic resistance gene is selected from the group of genes encoding hygromycin phosphotransferase, neomycin phosphotransferase, streptomycin phosphotransferase, and bleomycin-binding protein. In another embodiment, the selectable marker gene is a herbicide resistance gene. In another embodiment, the herbicide resistance gene is selected from the group of genes encoding 5-enolpyruvylshikimate-3-phosphate synthase, glyphosate oxidoreductase, glyphosate-N-acetyltransferase, and phosphinothricin acetyl transferase.

In another embodiment, the step of cultivating the seedling comprises (i) transferring the *Agrobacterium*-transformed seedling to soil and exposing the transformed seedling to conditions that promote growth.

In another embodiment, the step of screening the plants for stable integration of the desired polynucleotide comprises (i) exposing the plants to a screening solution containing a substance that only plants that express the selectable marker gene are tolerant to; (ii) growing the plants to maturity and allowing the plants to produce T1 seedlings; (iii) transferring the T1 seedlings to soil; and (iv) exposing the seedlings to the screening solution.

In another embodiment, the step of infecting the germinating plant seedling comprises submerging the seedling into a solution comprising an *Agrobacterium* strain that contains the *Agrobacterium* transformation vector; and (b) vortexing the solution.

In another embodiment, the selectable marker gene is operably linked to a yeast ADH terminator.

In another embodiment, the promoter and the terminator naturally occur in plants.

In another embodiment, the desired polynucleotide is a plant gene.

In another embodiment, expression of the desired polynucleotide in method 2 confers a trait to plants that comprise the desired polynucleotide in their genomes, wherein the trait is selected from the group consisting of increased drought tolerance, reduced height, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved taste, improved texture, decreased phosphate content, increased germination, increased micronutrient uptake, improved starch composition, and improved flower longevity.

In one embodiment, the substance contained in the screening solution is hydrogen cyanamide.

In another aspect, a method ("method 3") is provided for modifying the expression of a functional gene in a plant cell comprising:

(a) constructing a first T-DNA or P-DNA that comprises a desired polynucleotide that is capable of modifying the expression of a functional gene in a plant cell;

(b) constructing a second T-DNA or P-DNA that comprises a selectable marker gene operably linked to a promoter and terminator, wherein the terminator does not naturally occur in plants;

(c) exposing germinating plant seedlings to one or more *Agrobacterium* strains that contain the first T-DNA or P-DNA and the second T-DNA or P-DNA;

(d) selecting only those transformed seedlings that transiently express the selectable marker gene; and (e) selecting from the seedlings of (d), a seedling that comprises in its genome the desired polynucleotide but not the selectable marker;

wherein expression of the desired polynucleotide in the seedling of (e) modifies the expression of a functional gene in a plant cell in the seedling.

In one preferred embodiment the germinating plant seedling is from a monocotyledenous plant. In another embodiment, the monocotyledenous plant is selected from the group consisting of turfgrass, wheat, maize, rice, oat, wheat, barley, orchid, iris, lily, onion, and sorghum. In another embodiment, the turfgrass is selected from the group consisting of *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra* commutata (fine fescue), *Cynodon* dactylon (common bermudagrass); *Pennisetum clandestinum* (kikuyugrass), *Stenotaphrum secundatum* (st. augustinegrass), *Zoysia japonica* (zoysiagrass), and *Dichondra micrantha*.

In another preferred embodiment, the germinating plant seedling is from a dicotyledenous plant. In one embodiment, the dicotyledenous plant is selected from the group consisting of cotton, tobacco, *Arabidopsis*, tomato, potato, sugar beet, broccoli, cassava, sweet potato, pepper, poinsettia, legumes, alfalfa, soybean, carrot, strawberry, lettuce, oak, maple, walnut, rose, mint, squash, daisy, geranium, and cactus.

In another embodiment, the expression of the desired polynucleotide in the stably transformed plant confers a trait to the plant selected from the group consisting of increased drought tolerance, reduced height, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved taste, improved texture, decreased phosphate content, increased germination, increased micronutrient uptake, improved starch composition, improved flower longevity, and production of novel proteins or peptides.

In a preferred embodiment, the desired polynucleotide is selected from the group consisting of a gene or part thereof, the 5'-untranslated region of the gene, the 3'-untranslated region of the gene, the leader sequence associated with the gene, or the trailer sequence associated with the gene.

In a preferred embodiment, the gene is selected from the group of genes encoding a peptide or protein displaying antifungal or antimicrobial activity such as alfalfa AFP and D4E1, a nutritional peptide or protein, a transcription factor such as CBF3, a receptor that binds to pathogen-derived ligands such as the disease resistance protein R1, a hemoglobin such as VhB, an oxidase such as polypenol oxidase, an enzyme of the lignin biosynthesis pathway, an enzyme of industrial value, or an antigen. Preferably, the desired polynucleotide is operably linked to a promoter and a terminator.

In a preferred embodiment, the sequences of the promoter and the terminator naturally occur in the genome of plants and organisms that produce, or are used in, edible food sources.

In one embodiment, a first vector carries the first T-DNA or P-DNA and a second vector carries the second T-DNA or P-DNA.

In one other embodiment, the second vector comprises at least one of an omega-mutated virD2 polynucleotide, a codA polynucleotide, and a codA::upp fusion polynucleotide.

The present invention contemplates transgenic plants and their progeny, that are produced by any of the methods described herein.

In another aspect of the invention, a method ("method 4") for producing a transgenic plant is provided, comprising: (A) infecting a germinating plant seedling with an *Agrobacterium* transformation vector that comprises (i) a T-DNA or a P-DNA that comprises (a) the desired polynucleotide, and (b) a gene operably linked to a terminator that is not naturally expressed in plants, wherein the gene confers fertilizer tolerance to plants in which it is expressed; and (ii) a cytokinin gene, wherein the desired polynucleotide and the selectable marker gene are flanked by the border sequences of the T-DNA or by the border-like sequences of the P-DNA; (B) transferring the transformed seedling to soil and allowing them to grow into plants; (C) exposing the plants to 0.05% to 20% hydrogen cyanamide.

In one embodiment, the fertilizer tolerance gene confers resistance to cyanamide. In another embodiment, the selectable marker gene that confers resistance to cyanamide is selected from the group consisting of Cah, Cah homologs.

In another aspect, a method ("method 5") is provided for producing a transgenic plant, comprising (a) vortexing a solution comprising a germinating plant seedling and at least one *Agrobacterium* strain that harbors a vector carrying a desired polynucleotide; (b) transferring the *Agrobacterium*-transformed seedling to soil, and exposing the transformed seedling to conditions that promote growth; and (d) screening the plants to determine if the desired polynucleotide is integrated into the genome of at least one cell of the plant, wherein a plant comprising the desired polynucleotide in the genome is a transgenic plant.

In one preferred embodiment the germinating plant seedling is from a monocotyledenous plant. In another embodiment, the monocotyledenous plant is selected from the group consisting of turfgrass, wheat, maize, rice, oat, barley, orchid, iris, lily, onion, and sorghum. In another embodiment, the turfgrass is selected from the group consisting of *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra* commutata (fine fescue), *Cynodon* dactylon (common bermudagrass); *Pennisetum clandestinum* (kikuyugrass), *Stenotaphrum secundatum* (st. augustinegrass), *Zoysia japonica* (zoysiagrass), and *Dichondra micrantha*.

In another preferred embodiment, the germinating plant seedling is from a dicotyledenous plant. In one embodiment, the dicotyledenous plant is selected from the group consisting of cotton, tobacco, *Arabidopsis*, tomato, potato, sugar beet, broccoli, cassava, sweet potato, pepper, poinsettia, legumes, alfalfa, soybean, carrot, strawberry, lettuce, oak, maple, walnut, rose, mint, squash, daisy, geranium, and cactus.

In another embodiment, the expression of the desired polynucleotide in the stably transformed plant confers a trait to the plant selected from the group consisting of increased drought tolerance, reduced height, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved taste, improved texture, decreased phosphate content, increased germination, increased micronutrient uptake, improved starch composition, improved flower longevity, and production of novel proteins or peptides.

In a preferred embodiment, the desired polynucleotide of the present invention is selected from the group consisting of a gene or part thereof, the 5'-untranslated region of the gene, the 3'-untranslated region of the gene, the leader sequence associated with the gene, or the trailer sequence associated with the gene.

In a preferred embodiment, the gene is selected from the group of genes encoding a peptide or protein displaying antifungal or antimicrobial activity such as alfalfa AFP and D4E1, a nutritional peptide or protein, a transcription factor such as CBF3, a receptor that binds to pathogen-derived ligands such as the disease resistance protein R1, a hemoglobin such as VhB, an oxidase such as polypenol oxidase, an enzyme of the lignin biosynthesis pathway, an enzyme of industrial value, or an antigen.

In a preferred embodiment, the sequences of the promoter and the terminator naturally occur in the genome of plants, or are isolated from human food sources.

In a preferred embodiment, the vector used in method 5 may be the one that is described in detail above.

In one other embodiment, the step of screening comprises detecting the presence of the desired polynucleotide in cells of the transgenic plant.

In another embodiment, the method further comprises producing progeny from the transgenic plant and detecting the presence of the desired polynucleotide in cells of the progeny. In another embodiment, the border-like sequences of the P-DNA range in size from 20 to 100 by and share between 52% and 96% sequence identity with a T-DNA border sequence from *Agrobacterium tumafaciens*.

In another embodiment, expression of the selectable marker gene confers fertilizer tolerance to the transgenic plant and progeny thereof.

In another embodiment, the selectable marker gene that confers fertilizer tolerance is a selectable marker gene that confers resistance to cyanamide.

In another embodiment, the selectable marker gene that confers resistance to cyanamide is selected from the group consisting of Cah, Cah homologs. In another embodiment, the selectable marker gene is operably linked to a yeast ADH terminator. In another embodiment, the selectable marker gene is an antibiotic resistance gene. In yet another embodiment, the antibiotic resistance gene is selected from the group consisting of nptII or aph(3')II. In another embodiment, the selectable marker gene is a herbicide resistance gene. In another embodiment, the herbicide resistance gene is selected from the group consisting of GAT and EPSP synthase genes.

In one embodiment, the solution is vortexed from about 60 seconds to several hours. In another embodiment, the solution is vortexed for about 5 minutes to about 30 minutes.

In another aspect, a method ("method 6") is provided for producing a transgenic plant, comprising (a) vortexing a solution comprising a germinating plant seedling and at least one *Agrobacterium* strain that harbors a vector carrying a desired polynucleotide; (b) (i) producing callus from the transformed seedling; (iii) inducing shoot and root formation from the callus to produce a plantlet; (c) growing the plantlets into plants; and (d) screening the plants to determine if the desired polynucleotide is incorporated into the genome of at least one cell of the plant, wherein a plant comprising the desired polynucleotide in the genome is a transgenic plant.

In one preferred embodiment the germinating plant seedling is from a monocotyledenous plant. In another embodiment, the monocotyledenous plant is selected from the group consisting of turfgrass, wheat, maize, rice, oat, barley, orchid, iris, lily, onion, and sorghum. In another embodiment, the turfgrass is selected from the group consisting of *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra commutata* (fine fescue), *Cynodon dactylon* (common bermudagrass); *Pennisetum clandestinum* (kikuyugrass), *Stenotaphrum secundatum* (st. augustinegrass), *Zoysia japonica* (zoysiagrass), and *Dichondra micrantha*.

In another preferred embodiment, the germinating plant seedling is from a dicotyledenous plant. In one embodiment, the dicotyledenous plant is selected from the group consisting of cotton, tobacco, *Arabidopsis*, tomato, potato, sugar beet, broccoli, cassava, sweet potato, pepper, poinsettia, legumes, alfalfa, soybean, carrot, strawberry, lettuce, oak, maple, walnut, rose, mint, squash, daisy, geranium, and cactus.

In another embodiment, the expression of the desired polynucleotide in the stably transformed plant confers a trait to the plant selected from the group consisting of increased drought tolerance, reduced height, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved taste, improved texture, decreased phosphate content, increased germination, increased micronutrient uptake, improved starch composition, improved flower longevity, and production of novel proteins or peptides.

In a preferred embodiment, the desired polynucleotide of the present invention is selected from the group consisting of a gene or part thereof, the 5'-untranslated region of the gene, the 3'-untranslated region of the gene, the leader sequence associated with the gene, or the trailer sequence associated with the gene.

In a preferred embodiment, the gene is selected from the group consisting of D4E1 synthetic peptide gene, HOS1 gene homologs, the *Vitreoscilla* hemoglobin gene, and genes involved in the lignin biosynthetic pathway. Preferably, the desired polynucleotide is operably linked to a promoter and a terminator.

In a preferred embodiment, the sequences of the promoter and the terminator are isolated from the genome of human food sources.

In another embodiment, the vector comprises (a) a T-DNA or a P-DNA that comprises (i) the desired polynucleotide, and (ii) a selectable marker gene operably linked to a terminator that is not naturally expressed in plants; and (b) a backbone integration marker gene, wherein the desired polynucleotide and the selectable marker gene are positioned between the border sequences of the T-DNA or between the border-like sequences of the P-DNA, and wherein the backbone integration marker is not positioned within the T-DNA or within the P-DNA.

In another embodiment, the backbone integration marker gene is operably linked to a promoter and a terminator. In one embodiment, the backbone integration marker is a cytokinin gene. In yet another embodiment, the cytokinin gene is IPT, and the plant is a dicotyledon plant. In another embodiment, the backbone integration marker is PGA22, TZS, HOC1, CKI1, and ESR1.

In yet another embodiment, the border-like sequences of the P-DNA range in size from 20 to 100 by and share between 52% and 96% sequence identity with a T-DNA border sequence from *Agrobacterium tumafaciens*.

In another embodiment, expression of the selectable marker gene confers fertilizer tolerance to the transgenic plant and progeny thereof.

In another embodiment, the selectable marker gene that confers fertilizer tolerance is a selectable marker gene that confers resistance to cyanamide.

In another embodiment, the selectable marker gene that confers resistance to cyanamide is selected from the group consisting of CAH or CAH homologs derived from certain cyanamide tolerant soil fungi including *Aspergillus, Penicillium*, and *Cladosporium*. In another embodiment, the selectable marker gene is operably linked to a yeast ADH terminator. In another embodiment, the selectable marker gene is an antibiotic resistance gene. In yet another embodiment, the antibiotic resistance gene is selected from the group of genes encoding hygromycin phosphotransferase, neomycin phosphotransferase, streptomycin phosphotransferase, and bleomycin-binding protein. In another embodiment, the selectable marker gene is a herbicide resistance gene. In another embodiment, the herbicide resistance gene is selected from the group of genes encoding 5-enolpyruvylshikimate-3-phosphate synthase, glyphosate oxidoreductase, glyphosate-N-acetyltransferase, and phosphinothricin acetyl transferase.

In another embodiment, the step of screening comprises detecting the presence of the desired polynucleotide in cells of the transgenic plant.

In another embodiment, the method comprises producing progeny from the transgenic plant and detecting the presence of the desired polynucleotide in cells of the progeny.

In one other embodiment, the solution is vortexed from about 60 seconds to several hours. In another embodiment, the solution is vortexed for about 5 minutes to about 30 minutes.

The method, in another embodiment, further comprises the step of growing the seedling of (e) into a plant, wherein the plant is a transformed plant and wherein at least one cell of the transformed plant comprises in its genome the desired polynucleotide.

In another embodiment, the method further comprises crossing the transformed plant with a non-transformed plant to produce at least one progeny plant that comprises the desired polynucleotide in its genome.

In another embodiment, the method further comprises selfing the transformed plant to produce at least one progeny plant that comprises the desired polynucleotide in its genome.

According to the invention, the desired polynucleotide is operably linked to a promoter and a terminator. In one embodiment, the desired polynucleotide consists essentially of a sequence that is native to the selected plant, native to a plant from the same species, or is native to a plant that is sexually interfertile with the selected plant. In another embodiment, the desired polynucleotide, the promoter, and the terminator consist essentially of sequences that are endogenous to a sequence naturally found in a plant or derived from a food source.

In another embodiment, the modification of expression of a functional gene results in the modification of a trait to plants that comprise the desired polynucleotide in their genomes, wherein the trait is selected from the group consisting of increased drought tolerance, reduced height, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved taste, improved texture, decreased phosphate content, increased germination, increased micronutrient uptake, improved starch composition, improved flower longevity, and production of novel proteins or peptides.

In one other embodiment, the first vector and the second vector are both present in the same strain of *Agrobacterium*.

In another embodiment, the first vector is present in a first strain of *Agrobacterium* and the second vector is present in a second, different strain of *Agrobacterium*

In another aspect, the invention provides a method ("method 7") for identifying promoters that function in plant cells, comprising:

(a) creating *Agrobacterium* binary vectors that each comprise an plant-derived polynucleotide that is operably linked to a Cah gene;

(b) infecting a germinating plant seedling with *Agrobacterium* strains comprising the binary vectors;

(c) transferring the transformed seedling to media that comprises cyanamide and allowing the seedling to form calli, wherein only seedling that can express the Cah gene will form calli;

(d) transferring cyanamide resistant calli to shoot-inducing medium, and isolating DNA from resultant shoots; and (e) identifying the sequence of the artificial polynucleotide driving expression of the Cah gene, wherein the sequence of the plant-derived polynucleotide represents the sequence of a synthetic promoter.

In another embodiment, the present invention contemplates a CAH gene homolog with the sequence of SEQ ID NO. 1, and variants thereof, which confer resistance to cyanamide.

In another embodiment, the present invention encompasses a terminator sequence that is associated with the rice actin-1 gene described in SEQ ID NO. 6, and variants thereof, which function as a terminator.

In another embodiment, the present invention contemplates a plant-like promoter gene with the sequence of SEQ ID NO. 9, and variants thereof, which function as a promoter.

Thus, the present invention encompasses a polynucleotide that has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to SEQ ID NO. 1, and which encodes a protein that is cyanamide tolerant. Variants that have less than 60% sequence identity to SEQ ID NO. 1, but which also encode functional cyanamide tolerant proteins are also encompassed by the present invention.

The present invention encompasses a polynucleotide that has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to SEQ ID NO. 6, and which encodes a functional terminator. Variants that have less than 60% sequence identity to SEQ ID NO. 6, but which also encode functional terminators are also encompassed by the present invention.

The present invention encompasses a polynucleotide that has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to SEQ ID NO. 9, and which encodes a promoter that is functional in plants. Variants that have less than 60% sequence identity to SEQ ID NO. 9, but which also encode functional promoters are also encompassed by the present invention.

The present invention also encompasses a polynucleotide comprises the sequence of any one of SEQ ID NOs. 1, 6, or 9. Furthermore, the present invention encompasses a polynucleotide consisting essentially of the sequence of any one of SEQ ID NOs. 1, 6, or 9. Finally, the present invention encompasses a polynucleotide consisting of the sequence of any one of SEQ ID NOs. 1, 6, or 9.

Thus, the present invention encompasses the use of the rice actin-1 terminator sequence (SEQ ID NO. 6) in a construct, operably linked to a desired polynucleotide, to terminate expression of a desired polynucleotide. Similarly, the sugarcane-like promoter (SEQ ID NO. 9) can be operably linked to a desired polynucleotide to express the desired polynucleotide.

In one other embodiment, the efficiency of stable transformation can be further enhanced by inducing double strand breaks in the chromosomes of germinating seedling before, during, and/or after infection. For instance, a plant tissue may be exposed to such a chemical compound one day prior to infection, and then again after infection for about 1 hour, about 2 or more hours, about 5 or more hours, about 10 or more hours, or one or more days. In one embodiment, double strand breaks are generated by subjecting seedlings to low doses of chemicals such as methyl methane sulfonate (MMS), HO-endonuclease, bleomycin, neocarzinostatin, camptothecan, and cisplatin. In another embodiment, the seedling is exposed, before, during, or after infection to ionizing radiation or heavy ions.

Accordingly, in another aspect, methods of the present invention can be adapted to include a step that induces a double strand break in the plant genome in order to increase the frequency of integration of the desired polynucleotide. In one embodiment, the inventive methodology may entail vortexing a plant tissue with an *Agrobacterium* vector to optimize transfer of the vector and desired polynucleotide(s) into plant cells, and also the induction of double stranded breaks in plant chromosomes to increase the frequency of stably transforming, i.e., integrating, the plant genome with the desired polynucleotide(s).

In another embodiment, the present invention is not limited to the transfer of nucleic acids into a plant cell by *Agrobacterium*-mediated transformation methods. Other methods, such as the inventive vortexing method, particle bombardment, polyethylene glycol treatment, liposomal delivery, microinjection, whiskers, and electroporation can be used in conjunction with the chemical compounds, or ionizing radiation or heavy ion exposure, described above for inducing double strand breaks in the plant chromosomal DNA. Accordingly, the present invention is not limited to only the combination of vortexing and induction of double strand breaks. For example, plant tissues may be transformed using whiskers combined with exposure to methyl methane sulfonate.

Furthermore, the DNA and/or desired polynucleotide to be transferred into the plant cell can be in the form of naked DNA, plasmid DNA, liposomal DNA, or coated onto beads, particles, whiskers, needles, or in any other formulation known to the skilled artisan.

BRIEF DESCRIPTION OF THE DRAWINGS

FIG. 2: Alignment of the CAH gene (SEQ ID NO: 33) from *Myrothecium verrucaria* with a new cyanamide tolerance gene (SEQ ID NO: 34) isolated from *Aspergillus* (CAN-H1) and a non-functional yeast CAH homolog (CAH-H2) (SEQ ID NO: 35)

FIG. 3: Alignment between a new ubiquitin-like promoter (UbiN) and the corresponding partial sequence of the sugarcane Ubiquitin-4 promoter

DETAILED DESCRIPTION OF THE PREFERRED EMBODIMENTS

The present invention provides methods for producing transgenic plants and transformation vectors.

The present inventive methods can be applied to many species of plants, including those that are difficult to transform by applying conventional transformation methods. The present invention provides methods for integrating a desired polynucleotide into a plant genome to alter the expression of a plant trait, or to produce a product, such as a pharmaceutically relevant or important protein, and methods for readily selecting and screening for cells and plants that comprise the desired polynucleotide in their genome.

In particular, the inventive transformation methods include transforming germinating seedling with a vector comprising a desired polynucleotide, and then either (1) planting the seedling directly into soil; (2) transferring the seedling to culture media, without inducing a callus phase, and then planting the seedling directly into soil; or (3) transferring the seedling to culture media, inducing a callus phase, and shoot and root formation, and then planting the seedling directly into soil.

FIG. 1 illustrates such methods. Plant tissues (FIG. 1, box "(a)") may be transformed by vortexing (FIG. 1, box "(c)"), and then planted directly into soil (FIG. 1, box "(e)") and then grown into the desired transgenic plant (FIG. 1, box "(h)").

Alternatively, after vortexing (FIG. 1, box "(c)"), the transformed plant tissues may be nurtured on tissue culture medium (FIG. 1, box "(d)"), planted directly into soil (FIG. 1, box "(e)"), and then grown into the desired transgenic plant (FIG. 1, box "(h)").

Finally, after vortexing, and nurturing on tissue culture medium, the plant tissue can be induced to undergo callus formation (FIG. 1, box "(g)"), and shoot and root growth, prior to being grown into the desired transgenic plant.

The inventive *Agrobacterium* vector that can be used in any one of such methods is illustrated in FIG. 1, box "("f)". The vector may, or may not, include a selectable/screenable marker for identifying transformed, transgenic plants, parts thereof, or transformed cells. For instance, when a plant tissue, such as a seedling, is transformed according to the present methods and planted directly into soil without the induction of a callus phase, the vector does not need to contain a selectable marker gene. Alternatively, after culturing the transformed seedling, or other plant tissue, on callus-inducing tissue culture media, one may select for successful transformants by including in the tissue media, a substance(s) to which only plant cells that contain a selectable marker gene are resistant to, or can tolerate.

The present invention uses terms and phrases that are well known to those practicing the art. Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described herein are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology (Sambrook & Russel, Molecular Cloning: A Laboratory Manual, 3rd ed., Cold Spring Harbor Laboratory Press, Cold Spring Harbor, N.Y., 2001).

Agitation: "agitiation" means to cause movement with violence or sudden force. With respect to the present invention, "agitation" refers to a violent and sudden physical vibration of a solution. "Agitation," as used herein, does not encompass the disruption of a solution by treatment with high-frequency sound waves, such as those produced by sonication.

*Agrobacterium*: as is well known in the field, *Agrobacteria* that are used for transforming plant cells, are disarmed and virulent derivatives of, usually, *Agrobacterium tumefaciens* or *Agrobacterium rhizogenes* that contain a vector. The vector typically contains a desired polynucleotide that is located between the borders of a T-DNA or, according to the present invention, between the border-like sequences of a "plant-DNA" ("P-DNA"), see definition below, which border (like) sequences are capable of transferring the desired polynucleotide into a plant genome.

Border and Border-like sequences: "border sequences" are specific *Agrobacterium*-derived sequences. Typically, a left border sequence and a right border sequence flank a T-DNA and function as recognition sites for virD2-catalyzed nicking reactions. The sequences of the left and right border sequences may or may not be identical. Their sequences may or may not be inverted repeats of one another. Such activity releases nucleic acid that is positioned between such borders. See Table 1 below for examples of border sequences. The released nucleic acid, complexed with virD2 and virE2, is targeted to plant cell nuclei where the nucleic acid is often integrated into the genome of the plant cell. Usually, two border sequences, a left-border and a right-border, are used to integrate a nucleotide sequence that is located between them into another nucleotide sequence. It is also possible to use only one border, or more than two borders, to accomplish integration of a desired nucleic acid in such fashion.

According to the present invention, a "border-like" sequence is isolated from a plant, and functions like the border sequence of an *Agrobacterium*-derived T-DNA. That is, a border-like sequence of the present invention promotes and facilitates the transfer of a polynucleotide to which it is linked from *Agrobacterium* to plant cell nuclei, and the subsequent stable integration of this polynucleotide into the plant genome. A plant-DNA, i.e., P-DNA, of the present invention preferably is delineated by border-like sequences.

A border-like sequence of a P-DNA is between 5-100 by in length, 10-80 by in length, 15-75 by in length, 15-60 by in length, 15-50 by in length, 15-40 by in length, 15-30 by in length, 16-30 by in length, 20-30 by in length, 21-30 by in length, 22-30 by in length, 23-30 by in length, 24-30 by in length, 25-30 by in length, or 26-30 by in length.

Figure 1:
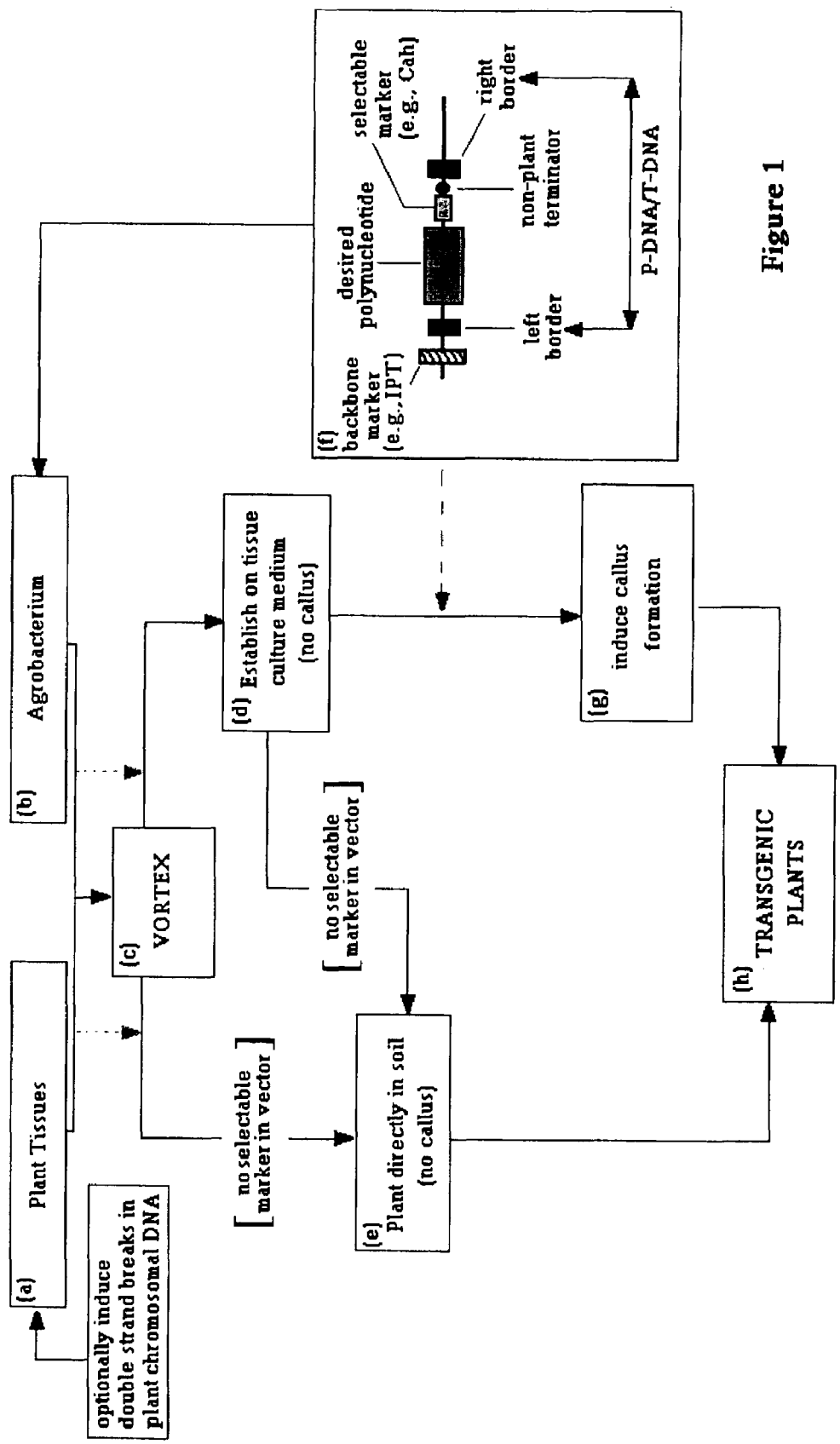
FIG. 1: Schematic flowchart of the inventive methods and compositions.

The border-like sequences of the present invention can be isolated from any plant. See SEQ ID NO.: 3 for a DNA fragment isolated from potato that contains, at either end, a border-like sequence. Thus, P-DNA border-like sequences of use for the present invention are isolated from a plant. A P-DNA border-like sequence is not identical in nucleotide sequence to any known *Agrobacterium*-derived T-DNA border sequence. Thus, a P-DNA border-like sequence may possess 1, 2, 3, 4, 5, 6, 7, 8, 9, 10, 11, 12, 13, 14, 15, 16, 17, 18, 19, 20, or more nucleotides that are different from a T-DNA border sequence from an *Agrobacterium* species, such as *Agrobacterium tumefaciens* or *Agrobacterium rhizogenes*. That is, a P-DNA border, or a border-like sequence of the present invention has at least 95%, at least 90%, at least 80%, at least 75%, at least 70%, at least 60% or at least 50% sequence identity with a T-DNA border sequence from an *Agrobacterium* species, such as *Agrobacterium tumefaciens* or *Agrobacterium rhizogenes*, but not 100% sequence identity. As used herein, the descriptive terms "P-DNA border" and "P-DNA border-like" are exchangeable.

A native P-DNA border sequence is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51% or 50% similar in nucleotide sequence to a *Agrobacterium* a T-DNA border sequence. A border-like sequence can, therefore, be isolated from a plant genome and be modified or mutated to change the efficiency by which they are capable of integrating a nucleotide sequence into another nucleotide sequence. Other polynucleotide sequences may be added to or incorporated within a border-like sequence of the present invention. Thus, a P-DNA left border or a P-DNA right border may be modified so as to possess 5'- and 3'-multiple cloning sites, or additional restriction sites. A P-DNA border sequence may be modified to increase the likelihood that backbone DNA from the accompanying vector is not integrated into the plant genome.

Table 1 below depicts the sequences of known T-DNA border sequences and sequences identified herein as border-like sequences. By aligning sequences with known T-DNA border sequences, new "border-like" sequences were identified that existed in plant genomes. The "potato" border-like sequences of Table 1 were isolated herein, using degenerate primers in polymerase chain reactions on potato genomic template DNA. The present invention encompasses the use of such potato P-DNA border-like elements for transferring a desired polynucleotide into the genome of a plant cell.

TABLE 1

"Border" and "Border-Like" sequences

*Agrobacterium* T-DNA borders

| Sequence | Source |
|---|---|
| TGACAGGATATATTGGCGGGTAAAC (SEQ ID NO. 12) | Agro. nopaline strains (RB) |
| TGGCAGGATATATTGTGGTGTAAAC (SEQ ID NO. 13) | Agro. nopaline strains (LB) |
| TGGCAGGATATATACCGTTGTAATT (SEQ ID NO. 14) | Agro. octopine strains (RB) |
| CGGCAGGATATATTCAATTGTAATT (SEQ ID NO. 15) | Agro. octopine strains (LB) |
| TGGTAGGATATATACCGTTGTAATT (SEQ ID NO. 16) | LB mutant |
| TGGCAGGATATATGGTACTGTAATT (SEQ ID NO. 17) | LB mutant |
| YGRYAGGATATATWSNVBKGTAAWY (SEQ ID NO. 18) | Border motif |

Border-like sequences

| Sequence | Source |
|---|---|
| TGACAGGATATATGGTAATGTAAAC (SEQ ID NO. 19) | potato (border-like sequence)* |
| TGGCAGGATATATACCGATGTAAAC (SEQ ID NO. 20) | potato (border-like sequence)* |

Y = C or T; R = A or G; K = G or T; M = A or C; W = A or T; S = C or G; V = A, C, or G; B = C, G, or T.
*potato border-like sequences were obtained and isolated according to the presently-described inventive methods.

Callus formation: typically, young roots, stems, buds, and germinating seedlings are a few of the sources of plant tissue that can be used to induce callus formation. Callus formation is controlled by growth regulating substances present in tissue culture medium, such as auxins and cytokinins. The specific substances, and concentrations of those substances, that induce callus formation varies between plant species. Occasionally, different sources of explants require different culturing conditions, even if obtained from the same plant or species. Accordingly, a cocktail of various growth substances can be added to tissue culture medium in order to induce callus formation from a variety of plant species that are incubated on such media. Other factors, such as the amount of light, temperature, and humidity, for instance, are important in establishing a callus. Once established, callus cultures can be used to obtain protoplasts, or study somatic embryogenesis, organogenesis, and secondary metabolite production.

The skilled artisan is well aware of various protocols, media, and conditions that can be modified to induce callus formation from a particular explant. The FOOD AND AGRICULTURE ORGANIZATION OF THE UNITED NATIONS' Agricultural Services Bulletin No. 108, entitled, "PLANT TISSUE CULTURE: AN ALTERNATIVE FOR PRODUCTION OF USEFUL METABOLITE" by Masanaru Misawa of Bio International Inc., Toronto, Canada (http://www.fao.org/docrep/t0831e/t0831e00.htm#con) lists such conditions in Chapter 4. There, one learns that the successful production of callus depends upon plant species and their qualities. Dicotyledons, for example, are quite amenable to callus formation, compared to monocotyledons. Suitable tissue culture media for inducing callus formation from an explant may include inorganic salts, carbon sources, vitamins, phytohormones, and organic supplements. See for additional information: Plant Cell Tissue and Organ Culture, Fundamental Methods, Gamborg and Phillips, eds, 1995 (Springer Verlag, New York)

Desired Polynucleotide: a desired polynucleotide of the present invention is a genetic element, such as a promoter, enhancer, or terminator, or gene or polynucleotide that is to be transcribed and/or translated in a transformed cell that comprises the desired polynucleotide in its genome. If the desired polynucleotide comprises a sequence encoding a protein product, the coding region may be operably linked to regulatory elements, such as to a promoter and a terminator, that bring about expression of an associated messenger RNA transcript and/or a protein product encoded by the desired polynucleotide. Thus, a "desired polynucleotide" may comprise a gene that is operably linked in the 5'- to 3'-orientation, a promoter, a gene that encodes a protein, and a terminator. Alternatively, the desired polynucleotide may comprise a gene or fragment thereof, in an "antisense" orientation, the transcription of which produces nucleic acids that may form secondary structures that affect expression of an endogenous gene in the plant cell. A desired polynucleotide may also yield a double-stranded RNA product upon transcription that initiates RNA interference of a gene to which the desired polynucleotide is associated. A desired polynucleotide of the present invention may be positioned within a T-DNA or P-DNA, such that the left and right T-DNA border sequences, or the left and right border-like sequences of the P-DNA, flank or are on either side of the desired polynucleotide. The present invention envisions the stable integration of one or more desired polynucleotides into the genome of at least one plant cell. A desired polynucleotide may be mutated or a variant of its wild-type sequence. It is understood that all or part of the desired polynucleotide can be integrated into the genome of a plant. It also is understood that the term "desired polynucleotide" encompasses one or more of such polynucleotides. Thus, a P-DNA or T-DNA of the present invention may comprise one, two, three, four, five, six, seven, eight, nine, ten, or more desired polynucleotides.

According to the present invention, a desired polynucleotide also may be used to alter a trait (see definition below) associated with a plant. In a situation where the plant is a food crop for consumption, it is preferable that the plant is not transformed so as to integrate undesirable DNA into its genome. A desired polynucleotide also may be used for pharmaceutical purposes, to express in plants a product of pharmaceutical relevance or importance. In that situation, any foreign, native, or undesirable nucleic acids may be used to express the desired polynucleotide. Examples of pharmaceutically relevant desired polynucleotides include those that encode peptides, nutraceuticals, vaccines, growth factors, and enzymes.

Dicotyledonous plant (dicot): a flowering plant whose embryos have two seed halves or cotyledons. Examples of dicots include but are not limited to, cotton, tobacco, *Arabidopsis*, tomato, potato sugar beet, broccoli, cassava, sweet potato, pepper, poinsettia, bean, alfalfa, soybean, carrot, strawberry, lettuce, oak, maple, walnut, rose, mint, squash, daisy, geranium, avocado, and cactus.

Food source: the present invention contemplates to improve food crops by introducing DNA that is mainly or exclusively derived from human food sources into the genomes of these crops and plants. Examples of edible food sources preferably includes baker's yeast and plants that produce edible fruits, vegetables, and grains. Preferably, DNA is not obtained from animals, bacteria, viruses, and fungi. Accordingly, genetic elements such as promoters, terminators, genes, and selectable markers, introduced into a plant genome, may be preferably derived from, or isolated from, plants that produce edible foods or organisms, such as yeast.

Foreign: "foreign," with respect to a nucleic acid, means that that nucleic acid is derived from non-plant organisms, or derived from a plant that is not the same species as the plant to be transformed or is not derived from a plant that is not interfertile with the plant to be transformed, does not belong to the species of the target plant. According to the present invention, foreign DNA or RNA represents nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product. According to the present invention, a most desired transgenic plant is one that contains minimal, if any, foreign nucleic acids integrated into its genome. The present invention also encompasses transgenic plants that do contain non-plant species nucleic acids in their genomes.

Gene: A gene is a segment of a DNA molecule that contains all the information required for synthesis of a product, polypeptide chain or RNA molecule, that includes both coding and non-coding sequences.

Genetic element: a "genetic element" is any discreet nucleotide sequence such as, but not limited to, a promoter, gene, terminator, intron, enhancer, spacer, 5'-untranslated region, 3'-untranslated region, or recombinase recognition site.

Genetic modification: stable introduction of DNA into the genome of certain organisms by applying methods in molecular and cell biology.

Introduction: as used herein, refers to the insertion of a nucleic acid sequence into a cell, by methods including infection, transfection, transformation or transduction.

Monocotyledonous plant (monocot): a flowering plant whose embryos have one cotyledon or seed leaf. Examples of monocots include, but are not limited to turfgrass, maize, rice, oat, wheat, barley, sorghum, orchid, iris, lily, onion, and palm. Examples of turfgrass include, but are not limited to *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra* commutata (fine fescue), *Cynodon dactylon* (common bermudagrass varieties including Tifgreen, Tifway II, and Santa Ana, as well as hybrids thereof); *Pennisetum clandestinum* (kikuyugrass), *Stenotaphrum secundatum* (st. augustinegrass), *Zoysia japonica* (zoysiagrass), and *Dichondra micrantha*.

Native: a "native" genetic element refers to a nucleic acid that naturally exists in, originates from, or belongs to the genome of a plant that is to be transformed. Thus, any nucleic acid, gene, polynucleotide, DNA, RNA, mRNA, or cDNA molecule that is isolated either from the genome of a plant or plant species that is to be transformed, or is isolated from a plant or species that is sexually compatible, or interfertile with the plant species that is to be transformed, is "native" to, i.e., indigenous to, the plant species. In other words, a native genetic element represents all genetic material that is accessible to plant breeders for the improvement of plants through classical plant breeding. For instance, native DNA incorporated into cultivated potato (*Solanum tuberosum*) can be derived from any genotype of *S. tuberosum* or any genotype of a wild potato species that is sexually compatible with *S. tuberosum* (e.g., *S. demissum*). Any variants of a native nucleic acid also are considered "native" in accordance with the present invention. In this respect, a "native" nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence.

A "native" nucleic acid isolated from a plant may also encode a variant of the naturally occurring protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in amino acid sequence to the unmodified, native protein expressed in the plant from which the nucleic acid was isolated.

Naturally occurring nucleic acid: this phrase means that the nucleic acid is found within the genome of a selected plant species and may be a DNA molecule or an RNA molecule. The sequence of a restriction site that is normally present in the genome of a plant species can be engineered into an exogenous DNA molecule, such as a vector or oligonucleotide, even though that restriction site was not physically isolated from that genome. Thus, the present invention permits the synthetic creation of a nucleotide sequence, such as a restriction enzyme recognition sequence, so long as that sequence is naturally occurring in the genome of the selected plant species or in a plant that is sexually compatible with the selected plant species that is to be transformed.

Operably linked: combining two or more molecules in such a fashion that in combination they function properly in a plant cell. For instance, a promoter is operably linked to a structural gene when the promoter controls transcription of the structural gene.

P-DNA: according to the present invention, P-DNA ("plant-DNA") is isolated from a plant genome and comprises at each end, or at only one end, a T-DNA border-like sequence. Thus, a P-DNA may comprise a left border-like sequence and a right border-like sequence. The border-like sequences preferably share at least 50%, at least 60%, at least 70%, at least 75%, at least 80%, at least 90% or at least 95%, but less than 100% sequence identity, with a T-DNA border sequence from an *Agrobacterium* species, such as *Agrobacterium tumefaciens* or *Agrobacterium rhizogenes*. Thus, P-DNAs can be used instead of T-DNAs to transfer a desired polynucleotide from *Agrobacterium* to a plant chromosome. The desired polynucleotide may or may not be native to the plant species to be transformed. That is, a P-DNA may be used to transfer foreign, as well as native, nucleic acids into a plant cell. Accordingly, the vectors of the present invention can be used to transfer a desired polynucleotide of the present invention (see definition above for "desired polynucleotide") into a plant genome. It is understood that all or part of the P-DNA containing the desired polynucleotide can be integrated into a plant genome by *Agrobacterium*-mediated transformation.

A P-DNA may be modified to facilitate cloning and should preferably not naturally encode proteins or parts of proteins. The P-DNA can be modified to reduce the frequency of vector backbone integration into a transformed plant genome.

A P-DNA is characterized in that it contains, at each end, at least one border sequence, referred to herein as a P-DNA "border-like" sequence, because its sequence is similar to, but not identical with, conventional T-DNA border sequences. See the definition of a "border sequence" and "border-like" above.

A desired polynucleotide and selectable marker may be positioned between the left border-like sequence and the right border-like sequence of a P-DNA of the present invention. The desired polynucleotide of the present invention and a selectable marker may comprise a gene operably linked to a variety of different nucleic acids, such as to promoter and terminator regulatory elements that facilitate their expression, i.e., transcription and/or translation of the DNA sequence encoded by the desired polynucleotide or selectable marker.

Thus, the P-DNA of the present invention may be used to transfer foreign DNA into plant genomes, as well as polynucleotides that are endogenous to plants. Accordingly, the "desired polynucleotide" that is transferred to a plant genome can be foreign, or native, or from a food-source, and may represent a gene that is useful for producing a pharmaceutical product, such as a hormone or enzyme. The desired polynucleotide contained within the P-DNA also may be used to alter a trait associated with the transformed plant.

Plant tissue: a "plant" is any of various photosynthetic, eukaryotic, multicellular organisms of the kingdom Plantae characteristically producing embryos, containing chloroplasts, and having cellulose cell walls. A part of a plant, i.e., a "plant tissue" may be treated according to the methods of the present invention to produce a transgenic plant. Preferably, the plant tissue that is transformed using an *Agrobacterium*-derived vector is a germinating seedling. The inventive methods described herein, however, are not limited to the transformation of only germinating seedling. Other suitable plant tissues can be transformed according to the present invention and include, but are not limited to, pollen, leaves, stems, calli, stolons, microtubers, and shoots. Thus, the present invention envisions the transformation of angiosperm and gymnosperm plants such as turfgrass, wheat, maize, rice, barley, oat, sugar beet, potato, tomato, tobacco, alfalfa, lettuce, carrot, strawberry, cassava, sweet potato, geranium, soybean, oak, eucalyptus, walnut, and palm. According to the present invention "plant tissue" also encompasses plant cells. Plant cells include suspension cultures, callus, embryos, meristematic regions, callus tissue, leaves, roots, shoots, gametophytes, sporophytes, pollen, seeds and microspores. Plant tissues may be at various stages of maturity and may be grown in liquid or solid culture, or in soil or suitable media in pots, greenhouses or fields. A plant tissue also refers to any clone of such a plant, seed, progeny, propagule whether generated sexually or asexually, and descendents of any of these, such as cuttings or seed. Of particular interest are Kentucky bluegrass, creeping bentgrass, maize, and wheat, and dicots such as cotton, tomato, lettuce, *Arabidopsis*, tobacco, and geranium.

Plant transformation and cell culture: broadly refers to the process by which plant cells are genetically modified and transferred to an appropriate plant culture medium for maintenance, further growth, and/or further development. Such methods are well known to the skilled artisan.

Progeny: a "progeny" of the present invention, such as the progeny of a transgenic plant, is one that is born of, begotten by, or derived from a plant or the transgenic plant. Thus, a "progeny" plant, i.e., an "F1" generation plant is an offspring or a descendant of the transgenic plant produced by the inventive methods. A progeny of a transgenic plant may contain in at least one, some, or all of its cell genomes, the desired polynucleotide that was integrated into a cell of the parent transgenic plant by the methods described herein. Thus, the desired polynucleotide is "transmitted" or "inherited" by the progeny plant. The desired polynucleotide that is so inherited in the progeny plant may reside within a P-DNA or T-DNA construct, which also is inherited by the progeny plant from its parent. The term "progeny" as used herein, also may be considered to be the offspring or descendants of a group of plants.

Seed: a "seed" may be regarded as a ripened plant ovule containing an embryo, and a propagative part of a plant, as a tuber or spore. Seed may be incubated prior to *Agrobacte-*

*rium*-mediated transformation, in the dark, for instance, to facilitate germination. Seed also may be sterilized prior to incubation, such as by brief treatment with bleach. The resultant seedling can then be exposed to a desired strain of *Agrobacterium*.

Seedling: a young plant that is grown from a seed. Certain parts of a seedling, such as part or all of the scutellum may be removed prior to exposing the seedling to a solution comprising an *Agrobacterium* strain.

Selectable/screenable marker: a gene that, if expressed in plants or plant tissues, makes it possible to distinguish them from other plants or plant tissues that do not express that gene. Screening procedures may require assays for expression of proteins encoded by the screenable marker gene. Examples of such markers include the beta glucuronidase (GUS) gene and the luciferase (LUX) gene. The instant invention demonstrates that cyanamide tolerance genes such as CAH can also be used as a marker. Thus, a gene encoding resistance to a fertilizer, antibiotic, herbicide or toxic compound can be used to identify transformation events. Examples of selectable markers include the cyanamide hydratase gene (CAH) streptomycin phosphotransferase (SPT) gene encoding streptomycin resistance, the neomycin phosphotransferase (NPTII) gene encoding kanamycin and geneticin resistance, the hygromycin phosphotransferase (HPT or APHIV) gene encoding resistance to hygromycin, acetolactate synthase (als) genes encoding resistance to sulfonylurea-type herbicides, genes (BAR and/or PAT) coding for resistance to herbicides which act to inhibit the action of glutamine synthase such as phosphinothricin (Liberty or Basta), or other similar genes known in the art.

Sequence identity: as used herein, "sequence identity" or "identity" in the context of two nucleic acid or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237-244 (1988); Higgins and Sharp, *CABIOS* 5: 151-153 (1989); Corpet, et al., *Nucleic Acids Research* 16: 10881-90 (1988); Huang, et al., *Computer Applications in the Biosciences* 8: 155-65 (1992), and Pearson, et al., *Methods in Molecular Biology* 24: 307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995); Altschul et al., *J. Mol. Biol.*, 215:403-410 (1990); and, Altschul et al., *Nucleic Acids Res.* 25:3389-3402 (1997).

Software for performing BLAST analyses is publicly available, e.g., through the National Center for Biotechnology Information (http://www.ncbi.nlm.nih.gov/). This algorithm involves first identifying high scoring sequence pairs (HSPS) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPS containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters can be employed alone or in combination.

Multiple alignment of the sequences can be performed using the CLUSTAL method of alignment (Higgins and Sharp (1989) *CABIOS*. 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

Trait: a "trait" is a distinguishing feature or characteristic of a plant, which may be altered according to the present invention by integrating one or more "desired polynucleotides" and/or screenable/selectable markers into the genome of at least one plant cell of a transformed plant. The "desired polynucleotide(s)" and/or markers may confer a change in the trait of a tranformed plant, by modifying any one of a number of genetic, molecular, biochemical, physiological, morphological, or agronomic characteristics or properties of the transformed plant cell or plant as a whole. Thus, expression of one or more, stably integrated desired polynucleotide(s) in a plant genome, may alter a trait that is selected from the group consisting of, but not limited to, increased drought tolerance, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved vigor, improved taste, improved texture, decreased phosphate content, increased germination, increased micronutrient uptake, improved starch composition, and improved flower longevity.

Transcription and translation terminators: The expression vectors of the present invention typically have a transcriptional termination region at the opposite end from the transcription initiation regulatory region. The transcriptional termination region may be selected, for stability of the mRNA to enhance expression and/or for the addition of polyadenylation tails added to the gene transcription product.

Transfer DNA (T-DNA): an *Agrobacterium* T-DNA is a genetic element that is well-known as an element capable of integrating a nucleotide sequence contained within its borders into another nucleotide. In this respect, a T-DNA is flanked, typically, by two "border" sequences. A desired polynucleotide of the present invention and a selectable marker may be positioned between the left border-like sequence and the right border-like sequence of a T-DNA. The desired polynucleotide and selectable marker contained within the T-DNA may be operably linked to a variety of different, plant-specific (i.e., native), or foreign nucleic acids, like promoter and terminator regulatory elements that facilitate its expression, i.e., transcription and/or translation of the DNA sequence encoded by the desired polynucleotide or selectable marker.

Transformation of plant cells: A process by which a nucleic acid is stably inserted into the genome of a plant cell. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, microinjection, polyethylene glycol-treatment, heat shock, lipofection and particle bombardment.

Transgenic plant: a transgenic plant of the present invention is one that comprises at least one cell genome in which an exogenous nucleic acid has been stably integrated. According to the present invention, a transgenic plant is a plant that comprises only one genetically modified cell and cell genome, or is a plant that comprises some genetically modified cells, or is a plant in which all of the cells are genetically modified. A transgenic plant of the present invention may be one that comprises expression of the desired polynucleotide, i.e., the exogenous nucleic acid, in only certain parts of the plant. Thus, a transgenic plant may contain only genetically modified cells in certain parts of its structure.

Undesirable DNA: any DNA that is not derived from a common food source and is not essential for expression of a beneficial trait in a transgenic plant, when making a genetically engineered food crop. Under these circumstances, undesirable DNA is DNA from viruses, bacteria, fungi, animals, and non-edible plants.

Vortexing, turbo-vortexing: either term refers to the abrupt agitation of plant tissues, such as germinating seedling, using a standard vortex or other device. According to the present invention, plant tissues may be vortexed from 60 seconds to several hours. Preferably, the plant tissue is vortexed for about 5 to about 30 minutes. It is well within the purview of the skilled artisan to determine a suitable length of time to vortex plant tissues from various monocotyledon and dicotyledon plant species.

Variant: a "variant," as used herein, is understood to mean a nucleotide or amino acid sequence that deviates from the standard, or given, nucleotide or amino acid sequence of a particular gene or protein. The terms, "isoform," "isotype," and "analog" also refer to "variant" forms of a nucleotide or an amino acid sequence. An amino acid sequence that is altered by the addition, removal or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. "Variant" may also refer to a "shuffled gene" such as those described in Maxygen-assigned patents. For instance, a variant of the present invention may include variants of sequences and desired polynucleotides that are modified according to the methods and rationale disclosed in U.S. Pat. No. 6,132, 970, which is incorporated herein by reference.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

A surprising discovery of the present invention is that a germinating seedling that is agitated in a solution containing *Agrobacterium* cells harboring a vector that contains a desired polynucleotide can be planted into soil according to the methods described herein, and grown into a plant that contains cells that are stably transformed with the desired polynucleotide. Accordingly, the first, most basic method of the present invention entails vortexing germinating seedling with an *Agrobacterium* strain containing an appropriate vector, and then simply planting the vortexed seedling in soil, under conditions that promote growth.

The efficiency of stable transformation can be further enhanced by inducing double strand breaks in the chromosomes of germinating seedling before, during, and/or after infection. Such double strand breaks can be generated by, for instance, subjecting seedlings to low doses of chemicals such as methyl methane sulfonate (MMS), HO-endonuclease, bleomycin, neocarzinostatin, camptothecan, and cisplatin, or by using ionizing radiation or heavy ions. Similar effects may also be accomplished by temporarily blocking the cell's own double strand gap repair mechanism. Mutations that may inadvertently arise from these treatments can be easily removed by back-crossing transgenic plants with untransformed plants.

Accordingly, the inventive methodology may entail vortexing a plant tissue with an *Agrobacterium* vector to optimize transfer of the vector and desired polynucleotide(s) into plant cells, and also the induction of double stranded breaks in plant chromosomes to increase the frequency of stably transforming, i.e., integrating, the plant genome with the desired polynucleotide(s).

The transgenic plant is crossed or self-fertilized to transmit the desired gene or nucleotide sequence to progeny plants. Seedlings of this next generation of transgenic plants can be screened for the presence of a desired polynucleotide using standard techniques such as PCR, enzyme or phenotypic assays, ELISA, or Western blot analysis. Alternatively, if the transformation vector comprises a selectable/screenable marker(s), the plant progeny may be selected for resistance or tolerance to a particular substance, as is described in detail below. While vortexing is a preferred method of exposing plant tissues to *Agrobacterium* strains, the present invention is not limited to such a method.

The second method entails transferring the *Agrobacterium*-transformed seedling to soil only after the seedling has been nurtured on minimal tissue culture medium (e.g. MS—Murashige & Skoog, *Physiol. Plant,* 15: 473-479, 1962), without the induction of a callus. The "pre-planting" nurturing step helps to boost the strength, nutrients, and resources available to the seedling prior to planting directly in soil.

The third inventive method encompasses inducing the transformed seedling to undergo a callus phase, stimulating the growth of shoots and roots, and then planting directly in soil. To perform the latter, the present invention provides a novel *Agrobacterium* transformation vector, that may, or may not, be used in conjunction with the novel vortex method for transforming seedlings.

The novel transformation vector of the present invention comprises an alternative to the *Agrobacterium*-derived T-DNA element, which is characterized by a "left border" at its 5'-end, and a "right border" at its 3'-end. According to the invention, the alternative transfer DNA may be isolated from an edible plant in order to minimize the quantity of undesirable nucleic acids introduced into the target plant genome. Such a plant transfer DNA (P-DNA) also is delineated by left and right border-like sequences that support the transfer of one polynucleotide into another. For the purposes of the present invention, either T-DNA or P-DNA constructs can be used to transfer a desired polynucleotide into a plant cell. The skilled artisan would understand that, in some instances, it is desirable to reduce the amount and number of undesirable genetic elements that are introduced into a plant genome via *Agrobacterium*-mediated transformation. Accordingly, the skilled artisan could use the P-DNA of the present invention in such instances, because the P-DNA, and its border-like sequences, is isolated from a plant genome.

According to the present invention, a desired polynucleotide is positioned within such a P-DNA or T-DNA and is operably linked to a promoter and a terminator, that can express it. In order to further minimize the quantity of foreign nucleic acid introduced into a plant genome after successful transformation, the promoter and terminator linked to the desired polynucleotide may be promoters and terminators that naturally occur in a plant genome.

If required, a selectable marker that confers a detectable trait to plant cells containing it, can be positioned within the T-DNA/P-DNA of the inventive vector. Such a selectable marker may encode proteins that confer tolerance to herbicides such as glyphosate-N-acetyltransferase (GAT) or 5-enolpyruvylshikimate-3-phosphate synthase (EPSPS). A preferred selectable marker gene confers antibiotic resistance to transgenic plants, such as the neomycin phosphotransferase gene. Another preferred selectable marker gene provides cyanamide tolerance. One example of a cyanamide tolerance gene is the *Myrothecium verrucaria* cyanamide hydratase (CAH) gene. The instant invention demonstrates that distant homologs of the CAH gene, derived from soil fungi such as *Aspergillus, Cladosporium,* and *Penicillium* (but not from the yeast species *Saccharomyces cereviseae*) also function as cyanamide tolerance genes.

Calcium cyanamide is an environment-friendly nitrogen fertilizer. Because nitrogen is released only gradually, it poses less risk of nitrate pollution to groundwater than do the popular urea-based or ammonium-nitrate-based fertilizers. Furthermore, it provides beneficial additional effects because both the lime and cyanamide breakdown products such as dicyandiamide limit growth of undesirable fungi and parasites including *Sclerotinia, Pythium, Erysiphe* and nematodes, whereas it stimulates growth of the beneficial fungi *Aspergillus* and *Penicillium*.

One reason calcium cyanamide is not widely used in agriculture is that it can only be applied pre-emergence. However, tolerance to cyanamide makes it possible now to apply cyanamide during and after emergence. By using cyanamide-tolerant transgenic plants, calcium cyanamide can be applied both as a pre- and post-emergence fertilizer to increase yield and quality of crops and other agronomically important plants.

Thus, the present invention provides a novel combination of cyanamide fertilizer and cyanamide-tolerant plants to reduce the prevalence of soil-borne fungi, nematodes and insects, thereby increasing crop yield and quality. Enhanced disease and pest control can be obtained by not only applying before emergence but also during the growth phase of the plant.

The post-emergence application of calcium cyanamide is also predicted to limit the growth of undesirable plants, such as weeds, that are not naturally cyanamide tolerant. Such an application would limit the growth of multiple weeds including annual bluegrass, goosegrass, crowfootgrass, dollarweed, purple nutsedge, torpedograss, *kyllinga*, and alligatorweed on lawns planted with cyanamide-tolerant turf grass.

The present invention eliminates the need for explant starting material, such as immature plant embryos. Thus the inventive methodology is species-independent, cost-effective, and less labor intensive, than conventional species-dependent methods that require selection, proliferation, and regeneration of individually transformed somatic cells.

Seedling Characteristics

The inventive methodology utilizes a seedling that has only just begun to germinate and which is characterized, in a monocotyledonous or dicotyledonous plant, by a just-emerging coleoptile or cotyledon at the surface of the seed coat.

There may be an optimal stage of cotyledon emergence, i.e., germination, in seeds that provides a high frequency of transformation. For tobacco seeds, for instance, a high level of transformation frequency via agitation is observed when the cotyledon is one-half to three-quarters emerged from the seed coat. The time it takes to establish the optimal cotyledon emergence stage will vary depending on the specific dicotyledon species and the environmental conditions during germination, such as light, moisture, temperature, and the emergence medium (soil, artificial medium, sand, etc.).

One skilled in the art would know how to systematically define these environmental parameters for each dicotyledon seed species in order to determine the optimal cotyledon emergence stage. In this fashion, one may optimize when to agitate a germinating seed so as to obtain a high frequency of transformation. One may quantify the level of transformation by monitoring transient GUS expression assays or by stable transformation. For monocotyledon plants, such as turf and wheat, one would develop a timing of transformation based upon optimal coleoptile emergence instead of cotyledon emergence.

A seedling that is at such an early-stage of germination will possess cells that are rapidly proliferating as the seed develops. Furthermore, certain cells of the coleoptile may be progenitors of germ line cells, which means that transforming these cells in particular will increase the likelihood of obtaining an inheritable, but artificial or modified, trait. Accordingly, the present invention makes use of this naturally-occurring state of cell multiplication and development by exposing these seedlings to an *Agrobacterium* vector that contains a gene or nucleotide sequence that the skilled artisan wishes to integrate into cells of the germinating seedling.

Agitation

In particular, a seedling that is characterized by a just-emerging coleoptile or cotyledon may be agitated in a solution that contains an *Agrobacterium* strain. For instance, such a seed may be placed into a tube or some other vessel that contains an *Agrobacterium* solution, which is then vortexed in a standard bench-top vortex for a short period of time. A tube containing a seedling in solution may be turbo-vortexed. Alternatively, the seedling may be submerged into a solution that is mixed for some period of time with a magnetic stir-bar using a standard bench-top mixing device.

Vortexing

The vortexing step described above may be enhanced by adding a small amount of sand to the *Agrobacterium*-containing solution. In experiments with tobacco and geranium, for example, the inclusion of a small amount of sand in the transfection solution during vortexing greatly increased the frequency of transformation. Other materials in place of sand that act in an abrasive fashion may be added to the *Agrobacterium*-containing transfection solution, such as, but not limited to, small glass beads, silicon, plastic grains, or stone. Turbo-vortexing also may be employed to facilitate transformation.

Depending on the size of the germinating seedling and the intensity of the agitation, different seedlings from different plant species, may be vortexed for different periods of time, such as anywhere from a few seconds, or 1-15 minutes, 5-10 minutes, 1-5 minutes, 15-20 minutes, an hour, or several hours. Small germinating seedlings from plants such as tobacco, turfgrass and *Arabidopsis*, for instance, may require less agitation than larger germinating seedlings such as wheat, maize and cotton.

Removing Plants that Comprise Vector Backbone Sequences

It is possible that DNA from the vector portion flanking the P-DNA or T-DNA of a transformation construct is incorporated into the host plant genome while agitating a germinating seed in the *Agrobacterium*-containing transformation solution. Thus, it is necessary to distinguish plants that contain only the desired polynucleotide insert integrated into their genome and from plants that also contain regions of the plasmid vector (i.e., "backbone DNA") after transformation. Backbone DNA is the part of an *Agrobacterium* binary vector that excludes the T-DNA/P-DNA.

In order to facilitate identification of plants that contain backbone DNA, a "backbone integration marker," which alters some morphological feature of the plant, is placed upstream and/or downstream of the T-DNA/P-DNA. Thus, it is possible a backbone integration marker gene that changes the shape of the transformed plant's leaves, roots, stem, height or some other morphological feature, that is not attributable to an effect of the desired polynucleotide, can be used to identify plants that contain vector backbone sequences. The color, texture or other traits of a plant may be similarly altered. "Morphological" refers to the form and structure of an organism without particular consideration of function, or which relates directly to the form and structure of an organism or its parts.

Thus, a transformed plant that has a morphologically altered feature as compared to a non-transformed or wild-type plant of that plant species, is indicative of a plant that contains backbone vector DNA in its genome.

Accordingly, an *Agrobacterium* vector may also carry an operable cytokinin gene upstream and/or downstream of the insertion DNA that will alter some morphological feature of the plant if it is integrated into the plant genome. Thus, it is straightforward to distinguish between desired and undesired transformation events. Transformed plants that exhibit such an altered morphological feature can be removed from the pool of desired plants, because they must contain undesirable, i.e., backbone, DNA sequences integrated into the genome. In this way, plant genomes that contain integrated and undesirable vector sequences, as well as an integrated desired polynucleotide, can be identified by detecting the expression of the cytokinin gene. Thus, transgenic plants produced by the method of the present invention that display a cytokinin-overproducing phenotype can be discarded, while those that are indistinguishable from untransformed plants can be maintained for further analysis. A preferred cytokinin gene is the *Agrobacterium* isopentenyl phosphotransferase (IPT) gene. Another cytokinin gene is, for instance, the *Agrobacterium* transzeatine synthase (TZS) gene. The present invention is not limited to the use of only a cytokinin gene. Any gene that alters a morphological feature of a plant can be used similarly.

Another strategy for identifying plants stably transformed with only desired DNA is to PCR amplify genomic DNA prepared from the plant using combination of primer pairs designed to the desired and to backbone vector DNA sequences. Genomes from plants that produce PCR products using primers designed to the backbone vector sequences are from plants that contain integrated backbone DNA.

Thus, by either using the expression of a gene to change a morphological feature of a plant, or by screening for stably integrated foreign DNA in a transformed plant, plants stably transformed with only desired DNA sequences can be identified and selected.

Similarly, while the stable integration of marker genes into the genomes of plant cells facilitates the identification of transformation events, such modifications of plant genomes are undesirable because marker genes usually represent foreign DNA that can be harmful to the plant, and to elements in the surrounding environment. Use of a marker gene can be avoided through modification of conventional *Agrobacterium*-based methods.

It is known that plant cells exposed during agitation to two different *Agrobacterium* strains, can receive T-DNAs from both strains. One of the *Agrobacterium* strains used for plant infection may contain a mutant virD2 gene. This mutant *Agrobacterium* strain is capable of transferring T-DNAs to plant nuclei but most of these T-DNAs will fail to integrate into the plant genome (Shurvinton et al., *Proc. Natl. Acad. Sci. U.S.A.*, 89: 11837-11841, 1992; Mysore et al., *Mol. Plant. Microbe Interact.*, 11: 668-683, 1998). The mutant *Agrobacterium* strain can further contain a marker gene such as the neomycin phosphotransferase (NP770 gene, operably linked to a promoter and followed by a termination signal, between T-DNA borders. Infection of explants with this mutant strain will result in temporary marker gene expression in some plant cells. Only plant cells that transiently express the marker gene are able to survive media that contain a selection agent such as kanamycin.

The virulent *Agrobacterium* strain that contains a wild-type virD2 gene carries the recombinant DNA molecule of interest but lacks a marker gene. Upon co-infection, some plant cells will contain both a non-integrating T-DNA with the marker gene and an integrating carrier DNA with the sequences of interest. In fact, 65% of tobacco cells containing at least one T-DNA derived from one of the strains have been shown to also contain at least one T-DNA from the other strain (De Neve et al., *Plant J.*, 11:15-29, 1997; De Buck et al., *Mol. Plant. Microbe Interact.*, 11: 449-57, 1998).

After about 5 to 10 days, the infected seedlings or explants are transferred to media lacking the selection agent to support further growth of events that had survived the temporary selection period. A significant percentage of these events contain the T-DNA carrying a recombinant DNA molecule of interest and lack the T-DNA with a selectable marker gene for transformation.

*Agrobacterium* strains that contain a functional virD2 gene instead of mutant virD2 for transient marker gene expression may also be used for selection of plant transformants. However, the frequency of obtaining genetically modified plants lacking a marker gene is generally low compared to use of the mutant virD2 gene.

Cells that transiently express a marker gene can be discriminated from cells that don't express such a gene using a variety of selection systems. However, not all these selection systems are equally suitable. In potato and tobacco, the most preferred selection agents are kanamycin (about 100 mg/L) and paramomycin (about 25-50 mg/L) because they arrest untransformed cells within 5 to 10 days. Other selection agents include hygromycin, glyphosate, glufosinate and cyanamide. The marker genes corresponding to these various agents encode neomycin phosphotransferase (NPTII) for kanamycin or paramomycin resistance, hygromycin phosphotransferase (HPTII) for resistance to hygromycin, 5-enolpyruvul-3-phosphoshikimic acid synthase (EPSPS) for glyphosate resistance, phosphinothricin acetyltransferase (PAT) for glufosinate resistance, and cyanamide hydratase (CAH) for cyanamide resistance.

An alternative way to develop transgenic plants lacking a selectable marker gene is based on excision of the marker gene cassette after plant transformation. Such excision can be accomplished by, e.g., placing a constitutively expressed marker gene together with an inducible Cre gene between two lox sites. Induction of the Cre gene would then in certain cases result in excision of all sequences between the lox sites. One example of an inducible promoter is the sunflower Ha hsp17.7 G4 promoter (Coca et al., *Plant Mol. Biol.*, 31: 863-76, 1996). By subjecting regenerating plantlets to a mild heat shock, induction of the heat shock promoter will lead to Cre gene expression and subsequent ejection of the region between the lox sites in some of the transformants.

The present invention contemplates the integration, for example, of any desired polynucleotide into a cell of a plant using the inventive methods. Particularly preferred desired polynucleotides of the present invention that can be integrated into a plant genome and expressed according to the methodologies described herein, include, but are not limited to, (i) the synthetic peptide gene D4E1 (U.S. Pat. No. 6,084,156; U.S. Pat. No. 6,018,102) to confer bacterial resistance to transgenic plants such as geranium; (ii) the HOS1 gene homologs to enhance cold, freezing and salt tolerance in transgenic plants through gene silencing (Lee et al., *Gene and Develop.*, 15: 912-924, 2001); (iii) the *Vitreoscilla* hemoglobin gene (U.S. Pat. No. 5,959,187) to develop greener and insect tolerant turfgrass that displays increased seed germination and enhanced vigor; and (iv) genes involved in the lignin biosynthetic pathway.

Other plant traits whose expression can be modified, introduced, reduced, or increased by integrating a foreign or native desired polynucleotide or variant thereof into a plant genome by the inventive methodology, include traits selected from the group consisting of, but not limited to, increased drought tolerance, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved vigor, improved taste, improved texture, decreased phosphate content, increased germination, increased micronutrient uptake, improved starch composition, and improved flower longevity.

The examples below are intended to illustrate but not limit the invention. While they are typical of those that might be used, other procedures known to those skilled in the art may be used.

EXAMPLES

Example 1

Development of a Species-Independent Method to Obtain Transgenic Plants without the Need for Plant Cell Proliferation and Regeneration Binary vectors that were created to develop a species-independent transformation method carry an intron-containing beta glucuronidase (GUS) gene (Genbank accession number AF354045) operably linked to a promoter and terminator. The MMV24P promoter of mirabilis mosaic virus (Maiti et al., U.S. Pat. No. 6,420,547, 2002), and the promoter of the sugarcane ubiquitin-4 gene (Albert and Wei, US Patent 20020046415A1, 2002) were used to transform dicotyledonous and monocotyledonous plants, respectively. The binary vectors were introduced into *Agrobacterium* by incubating competent LBA4404 cells (50 μL) with 1 μg of vector DNA for 5 minutes at 37° C., freezing for about 15 seconds in liquid nitrogen (about −196° C.), and incubating again at 37° C. for 5 minutes. After adding 1 mL of liquid broth (LB), the treated cells were grown for 3 hours at 28° C. and plated on LB/agar containing streptomycin (100 mg/L) and kanamycin (100 mg/L). The vector DNAs were then isolated from overnight cultures of individual LBA4404 colonies and examined by restriction analysis to confirm their integrity.

The resulting *Agrobacterium* strains were used to successfully transform eight different plant systems.

1. *Arabidopsis thaliana*

First, seed of the *Arabidopsis thaliana* ecotype Columbia was sterilized by turbo-vortexing with 20% bleach. The sterile seed was then incubated for 2 days at room temperature in the dark to allow germination. The germinating seedlings were then emerged into an *Agrobacterium* suspension, which was obtained by resuspending precipitated cells of an overnight-grown culture in MS medium to obtain an optical density of 0.6-0.75. The mixture was turbo-vortexed using a high-performance microcentrifuge tube attachment for the Vortex-Genie 2 Mixer (Part # SI-0563) manufactured by Scientific Industries, Inc., Airport Orville Drive, Bohemia, N.Y. 11716 at a speed setting of "4" for 5 to 30 minutes. The treated seedlings were transferred to either soil or MS medium not containing any hormones, and incubated at 25° C. After 3 weeks, plants were sampled to assay for GUS expression (Jefferson et al., *EMBO J.* 6: 3901-3907, 1987). Approximately 13% of tested plants (168 of 1274) displayed a blue color in significant portions of both petioles and leaves (Table 2). GUS assays on control plants that had been infected without vortexing were negative. A total of 10 randomly chosen GUS-positive plants were grown for 4 more weeks at 25° C. to allow seed set. The resulting seed was sterilized and germinated on MS medium, and progenies were then GUS assayed to determine the frequency of transgene transmission to the next generation. These analyses demonstrated that up to 78% of progeny plants represented stably transformed lines (Table 3).

2. *Nicotiana tabacum* (Tobacco)

Second, seed of the *Nicotiana tabacum* (tobacco) variety SR-1 was sterilized by turbo-vortexing with 20% bleach. The sterile seed was then incubated for 5 days at room temperature in the dark to allow germination. Seedlings were turbo-vortexed with *Agrobacterium* as described above. After 2 days of co-cultivation, the treated seedlings were transferred to either soil or MS medium not containing any hormones, and incubated for about 3 weeks at 25° C. Treated seedlings were then assayed for GUS expression. As shown in Table 4, a 5-minute vortex-period resulted in a frequency of GUS-expressing seedlings of approximately 7% (44 of 628 seedlings); a 30-minute vortex-period resulted in a slightly lower efficiency (Table 4). Four randomly chosen GUS-positive seedlings were grown for 12 more weeks at 25° C. to allow seed set. The resulting seed was sterilized and germinated on MS medium, and progenies were then GUS assayed to determine the frequency of transgene transmission to the next generation. To confirm the presence of the GUS gene, DNA was extracted from T1 seedlings and used to perform a PCR analysis. These phenotypic and molecular analyses demonstrated that 21% of the progeny plants represented stably transformed lines (Table 5).

3. *Gossypium hirsutum* (Cotton)

Third, seed of the *Gossypium hirsutum* (cotton) variety Coker-312 was sterilized by turbo-vortexing with 20% bleach. After removal of seed coat and cotyledons, the sterile seed was incubated for 2 days at room temperature in the dark to allow germination. Seedlings were then Agro-infected in a similar way as described above, except that turbo-mixing was carried out for 15 minutes. The treated seedlings were transferred to MS medium not containing any hormones, and incubated at 25° C. After 3 weeks, samples of individual seedlings were assayed for GUS expression. A very high percentage of these leaves (50%) developed an intense blue color in stems, petioles and leaves, indicating that a high proportion of cells stably expressed the GUS gene. These seedlings are allowed to grow into mature plants and set seed. The frequency of transformation events that is transmitted to the next generation can be determined by screening progeny plants for GUS expression. Approximately 5-75% of progeny plants is predicted to represent stably transformed lines.

4. *Lactuca sativa* (Lettuce)

Fourth, seed of the *Lactuca sativa* (lettuce) variety "Royal Oak Leaf" was sterilized, germinated for 3 days, and turbo-vortexed with *Agrobacterium* as described above. After 2 days of co-cultivation, the treated seedlings were transferred to MS medium not containing any hormones, and incubated for about 3 weeks at 25° C. Treated seedlings were then assayed for GUS expression. Seventy percent of lettuce seedlings displayed GUS activity, demonstrating that the marker-free transformation method is particularly effective in this crop system. About 5-75% of progeny plants are expected to contain a transmitted transgene.

5. *Lycopersicon esculentum* (Tomato)

Fifth, seed of the *Lycopersicon esculentum* (tomato) variety variety "Juliet hybrid" was sterilized, germinated for 4 days, and turbo-vortexed with *Agrobacterium* as described above. After 2 days of co-cultivation, the treated seedlings were transferred to MS medium not containing any hormones, and incubated for about 3 weeks at 25° C. Treated seedlings were then assayed for GUS expression. Ninety percent of tomato seedlings displayed GUS activity, demonstrating that the marker-free transformation method is particularly effective in this crop system. About 5-75% of progeny plants are expected to contain a transmitted transgene.

6. *Agrostis palustris* (Creeping Bentgrass)

Sixth, seed of the *Agrostis palustris* (creeping bentgrass) variety L-93 was sterilized by turbo-vortexing with 20% bleach. The sterile seed was incubated at room temperature in the dark to allow germination. After 1 week, the germinating seedlings were turbo-vortexed with *Agrobacterium* for approximately 30 minutes. The infected seedlings were transferred to either soil or MS medium not containing any hormones, and incubated at 25° C. At several time points, the seedlings were assayed for GUS expression. Three days post-infection, all seedlings displayed a uniformly blue color in all tissues, indicating that the GUS gene was transferred effectively to the nuclei of a large proportion of plant cells. Even after 3 weeks, a high frequency of seedlings (22 of 106) still displayed a blue color in all tissues, indicating that most or all the cells of these seedlings contained the GUS gene stably integrated in their genomes. The frequency of seedlings that developed at least some blue color at the latter time point was 35% (37 of 106). This experiment was repeated several times with similar results. Seedlings that tested positive for uniform GUS expression were grown for an additional three weeks and subsequently transferred to a vernalization chamber set at 2° C. After a 2-month incubation period, the plants can be transferred to another growth chamber, and grown for 2 months at 25° C. with a 16-hour photoperiod to allow flowering and seed set. The harvested progeny seed can be planted in soil, and 2-week old plants can be PCR analyzed for the presence of the GUS gene. Approximately 5-75% of progeny plants derived from GUS-positive T0 plants is predicted to contain the transmitted GUS gene.

7. *Triticum aestivum* (Wheat)

Seventh, seed of the *Triticum aestivum* (wheat) variety "Bobwhite" was sterilized by vortexing with 20% bleach. The sterile seed was incubated for 2 days at room temperature in the dark to allow germination. After removal of the scutellum, seedlings were turbo-vortexed with an *Agrobacterium* strain carrying the GUS vector. Surprisingly, these treated seedlings only comprising coleoptile and coleorhiza developed vigorously on MS medium not containing any hormones, and could be transferred to soil within three weeks. Almost all seedlings displayed a blue color after three days, indicating transient GUS gene expression. Approximately 4.5% of leaves still displayed large blue sectors on leaves and petioles, even after 3 weeks, indicating that many cells of these leaves contained the GUS gene stably integrated into their genomes. This experiment was repeated with similar results. GUS-positive seedlings were allowed to grow into mature plants and flower. DNA extracted from these flowers confirmed the presence of the GUS gene in at least some of the flower cells. Approximately 5-75% of progeny plants derived from GUS-positive flowers is predicted to contain the transmitted GUS gene.

8. *Zea mays* (Maize)

Eighth, seed of the recalcitrant *Zea mays* (maize) variety "Bonus" was sterilized by vortexing with 20% bleach. The sterile seed was incubated for 2 days at room temperature in the dark to allow germination. After removal of the scutellum, seedlings were infected with an *Agrobacterium* strain carrying pSIM115 or similar vectors. The treated seedlings were transferred to MS medium not containing any hormones, and incubated at 25° C. Of all seedlings transiently expressing the GUS gene three days after infection, about 5.5% still displayed an intense blue color 3 weeks later. Thus, a relatively high proportion of transferred DNAs succeeded in stably integrating into the plant genome. GUS-positive seedlings were transferred to the greenhouse, and are allowed to grow into flowering plants. PCR analysis is expected to confirm the presence of the GUS gene in about 5% of the flowers. Approximately 5-75% of progenies derived from these flowers are predicted to represent transgenic events.

The above experiments demonstrate that vortex-mediated seedling transformation is an effective and generally-applicable method to generate transgenic monocotyledonous and dicotyledonous plants. Transgenic plants developed through this species-independent method do not contain undesirable marker genes.

Example 2

Optimized Integration of Transferred DNAs

Example 1 demonstrates that the transfer of DNA from *Agrobacterium* to individual plant cell nuclei can be optimized for many different plant species by agitating seedlings in *Agrobacterium* suspensions. This example also shows that not all the transferred DNAs subsequently integrate into the plant cell genome. To optimize the second phase of the transformation process, 100 maize seedlings were infected as described in Example 1, and placed on media that contain low levels (50 parts per million) of methyl methane sulfonate (MMS), from 1 day prior to infection until 1 day after infection. An additional 100 seedlings were placed on control media that lack MMS. Approximately 2 weeks after infection, seedlings were assayed for stable GUS expression. Interestingly, 25% of MMS-treated seedlings contained multiple blue sectors on all assayed tissues whereas only 2.5% of control seedlings contained an occasional blue spot. Thus, the frequency of stable transformation can be increased at least 12.5-fold by using agents that trigger double strand breaks.

Example 3

Fertilizer Tolerance Genes as Screenable and Selectable Markers

As alternative to the transformation method described in Example 1, which eliminates the need for an undesirable marker gene, a transformation method that relies on the use of a marker gene was developed.

The first step in developing this method was to identify a gene that not only makes it possible to select or screen for transformed plant cells but one which also confers a new and beneficial trait to resulting transgenic plants. One example of such a gene provides herbicide tolerance. A more preferred example confers tolerance to cyanamide fertilizers. To identify sources of cyanamide tolerance, a selection of soil fungi were plated on potato dextrose agar (PDA) media containing 35 mg/L cyanamide. Fungi that grew vigorously on these media include *Aspergillus* sp., *Penicillium* sp., and *Cladosporium* sp.

A putative fungal cyanamide tolerance gene was amplified from *Aspergillus* DNA with HotMaster Taq DNA Polymerase (Eppendorf). The primer pair used in these reactions was 5'-TCTAGATGTCACAGTACGGATTTGTAAG-3' (SEQ ID NO: 21), and 5'-GGTCACCTCACTGCCCATCAGGGTGC-CGGCTTC-3' (SEQ ID NO: 22). The amplified fragments were both inserted into the yeast expression vector pNMT1-TOPO (Invitrogen) and the bacterial vector pGEM-T (Invitrogen). Sequence analysis of the new cyanamide tolerance gene inserted into pGEM-T (designated CAH-H1; see SEQ ID No.: 1) revealed less than 50% homology with both the previously identified *Myrothecium verrucaria* cyanamide hydratase (CAH) gene (Maier-Greiner et al., *Angew Chem Int Ed Engl*, 30: 1314-1315, 1991), and a CAH homolog of the highly cyanamide-sensitive species *Saccharomyces cereviseae* (FIG. 2). The PNMT1-TOPO vector carrying CAH-H1 was introduced into *Saccharomyces pombe* by using the S.c. EasyComp Transformation Kit (Invitrogen). Functional activity of the homolog was demonstrated by growing transformed cells on Edinburgh minimal medium (Invitrogen) containing 100 mg/L ampcilin and 50 mg/L cyanamide at 30° C. After 4 days, numerous colonies were observed on plates containing *S. pombe* cells transformed with pNMT1:CAH-H1, whereas no colonies were observed on pNMT1 control plates. The new cyanamide tolerance gene can be used as selectable marker gene for plant transformation by inserting it between a functional promoter and terminator, and introducing the resulting expression cassette into plant cells.

To develop transformation methods that include a screening step for cyanamide tolerance, vectors were created that contain the CAH gene (U.S. Pat. No. 6,268,547). *Agrobacterium* strains carrying such a fertilizer tolerance gene driven by the sugarcane ubiquitin-4 promoter were used to infect germinating bentgrass seedlings as described above. The infected seedlings were then planted in soil and allowed to grow for six weeks in a growth chamber (25° C. with a 16-hour photoperiod). The resulting plants were spray-treated with a 2% Dormex solution (Siemer and Associates Inc, Fresno, Calif.), which contains 1% hydrogen cyanamide.

About a third of the plants (84 of 250) displayed a high level of tolerance, whereas the remainder of the plants developed severe leaf necrosis. The cyanamide-tolerant plants were grown to maturity, and DNA was then extracted from flowers of these plants for PCR analysis. Using the CAH-specific primer pair 5'-CCA ACG GAT GGA CTG CCG TTC CAG TC 3' (SEQ ID NO: 23), and 5'-CAT GGA GTG ATT GTA GGT TTC GGG AC-3' (SEQ ID NO: 24), a 180-bp DNA fragment was amplified successfully from DNA of all of cyanamide-tolerant plants, indicating that the analyzed flowers contained the CAH gene stably integrated into the genomes of at least some of their cells. Thus, the data demonstrate that the CAH gene is an effective new screenable marker gene.

The eighty-four cyanamide-tolerant flowering plants were allowed to further mature and set seed. Progeny seedlings of some of these lines were planted in soil and analyzed for the presence of the CAH gene by performing PCR reactions on DNA isolated from these seedlings. This experiment demonstrated that an average of 20% of progeny plants contained the CAH gene stably integrated into their genomes (Table 6). Interestingly, this frequency is similar to those found for tobacco and *Arabidopsis* frequencies (21% and 53%, respectively), and implies the general applicability of vortex-mediated transformation methods that do not require a selection-step.

Seed of the more recalcitrant plant species *Poa pratensis* (Kentucky bluegrass) was also successfully transformed with the CAH-vector. Seed of the bluegrass variety Liberator was sterilized by turbo-vortexing with 20% bleach. The sterile seed was incubated for 6 days at room temperature in the dark to allow germination. Seedlings were infected with an *Agrobacterium* strain carrying the CAH gene as described in Example 2. The treated seedlings were transferred to soil and grown for 3 weeks at 25° C. with a 16-hour photoperiod. To screen for plants that contain the CAH gene in a significant portion of plant cells, plants were then sprayed with 2% Dormex. Approximately 10% (6 of 70) of plants displayed full tolerance to this spray-treatment. These plants are being vernalized and will be permitted to flower and set seed. Progenies will be tested phenotypically and molecularly to determine the frequency of plants that contain the CAH gene stably integrated into their genomes. This frequency is expected to be about 5-75%.

The method described above was slightly modified to include a selection step for cyanamide tolerance. Seed of the creeping bentgrass variety L-93 was sterilized, germinated, and infected with an *Agrobacterium* strain carrying a Cah-vector as described in Example 1. Instead of planting the treated seedlings into soil, they were transferred to tissue culture media containing auxin 2,4-D (2 mg/L) and cyanamide (37.5 mg/L), to induce callus formation, and to select for transformation events, respectively. Surprisingly, a large percentage of seedlings (20%) developed rapidly proliferating cyanamide-tolerant callus tissue on their shoot apices, mostly around the crown region, within about 4 weeks. These calli were transferred to new MS media with a lower concentration of 2,4-D (0.01 mg/L) to induce shoot formation. Emerging shoots that arose from calli within about two weeks were transferred to MS medium lacking 2,4-D to induce root formation. After two more weeks, sufficient root mass was established, and plantlets were transferred to soil. The resulting regenerated plants displayed high levels of tolerance to spray-treatment with Dormex, and were shown by PCR to contain the CAH gene stably integrated into their genomes. This is the first time that whole seedlings have been used effectively as 'explant' material for the efficient transformation and subsequent proliferation and regeneration of individual plant cells. Thirty-six cyanamide tolerant plants were vernalized and allowed to set seed. Progenies derived from 2 plants were assayed by PCR to confirm the transmission of the CAH gene to the next generation. As shown in Table 6, the majority of tested T1 plants (5 of 6) showed positive for the transgene, implying the efficacy of this transformation method (standard 3:1 segregation ratios predict a maximum of 75% transgene-transmission to selfed progenies).

The very high transformation efficiencies that can be obtained by using whole seedlings as explant material for vortex-mediated transformation make this a preferred method for applications that require high-throughput transformation procedures such as functional genomics. This method is also desirable for, for example, "proof-of-concept" experiments, and for projects related to the overexpression of pharmaceutical and nutraceutical proteins and peptides in plants.

Example 3

New Binary Vectors for Transformation of Plants

Current methods to express a foreign gene in crop plants result in the introduction of various nucleic acids that are derived from non-food sources. The introduction of such DNA in the food supply is undesirable and should be limited or avoided. The current invention provides tools and methods to (1) replace the *Agrobacterium*-derived T-DNA with a DNA fragment derived from a food source, (2) prevent transformation events that contain bacterial vector backbone sequences from developing into whole plants, (3) replace the frequently used nopaline synthase (nos) terminator derived from *Agrobacterium* with a terminator derived from a food source, and (4) replace frequently used virus promoters with promoters derived from food sources.

1. New Transfer DNA

The *Agrobacterium*-derived T-DNA is delineated by a 25-bp left-border (LB) and right-border (RB) repeat, which function as specific recognition sites for virD2-catalyzed nicking reaction (Schilperoort et al., U.S. Pat. No. 4,940,838, 1990). The single stranded DNA released by these nicking reactions is transferred to plant cell nuclei where it often successfully integrates into the plant genome. Advanced BLAST searches of public databases including those maintained by The National Center For Biotechnology Information and SANGER failed to identify any border sequences in plants. It was therefore necessary to consider plant DNA sequences that are similar but not identical to T-DNA borders, designated here as "border-like". The challenge in trying to replace T-DNA borders with border-like sequences is that border sequences are highly conserved (see Table 1). A large part of these sequences is also highly conserved in the nick regions of other bacterial DNA transfer systems such as that of IncP, PC194, and fX174, indicating that these sequences are essential for conjugative-like DNA transfer (Waters et al., *Proc Natl Acad Sci* 88: 1456-60, 1991). Because there are no reliable data on border sequence requirements, the entire border seems therefore important in the nicking process. A single study that attempted to address this issue by testing the efficacy of border mutants in supporting DNA transfer is unreliable because negative controls did not appear to function appropriately (van Haaren et al., *Plant Mol Biol* 13: 523-531, 1989). Furthermore, none of the results of this study were confirmed molecularly. Despite these concerns, two possibly effective border mutants are shown in Table 1 as well.

Based on the homology among border sequences, a T-DNA border motif was identified (Table 1). Although this motif comprises 13,824 variants, many of which may not function—or may be inadequate—in transferring DNA, it represents the broadest possible definition of what a T-DNA border sequence is or may be. This border motif was then used to search publicly available DNA databases for homologs using the "Motif Alignment and Search Tool" (Bailey and Gribskov, *Bioinformatics* 14: 48-54, 1998) and "advanced BLASTN" ("penalty for nucleotide mismatch"=−1; "expect"=105; Altschul et al., *Nucleic Acids Res* 25: 3389-3402, 1997). Again, these searches did not identify any identical matches in organisms other than *Agrobacterium*.

To try and increase the chance of isolating a plant DNA fragment containing border-like sequences that correspond to the border motif, DNA was isolated from 100 genetically diverse potato accessions (the so-called "core collection," provided by the US Potato Genebank, WI). This DNA was pooled and used as template for polymerase chain reactions using a variety of oligonucleotides designed to anneal to borders or border-like sequences. Amplified fragments were sequence analyzed, and the sequence was then confirmed using inverse PCR with nested primers. One of the potato DNA fragments that was of particular interest contains a novel sequence without any major open reading frames that is delineated by border-like sequences (Table 1). One of the border-like sequences of this fragment contains 5 mismatches with the closest T-DNA border homolog; the other border-like sequence contains 3 mismatches with the closest homolog. Although both sequences contain one mismatch with the border motif, they were tested for their ability to support DNA transfer. For that purpose, the fragment was first reduced in size to 0.4-kilo basepairs by carrying out an internal deletion (SEQ ID NO.: 2). The resulting fragment was designated "P-DNA" (plant DNA) to distinguish it from the *Agrobacterium*-derived T-DNA.

To test the efficacy of P-DNA transfer from *Agrobacterium* to plant cells, an expression cassette for the neomycin phosphotransferase (NPTII) gene was inserted within the P-DNA sequence, located on a T-DNA-free plasmid that can be maintained in both *E. coli* and *A. tumefaciens*. An *Agrobacterium* strain carrying the resulting vector was used to infect stem explants of 4-week-old in vitro grown plantlets of the potato variety Russet Ranger. The infected stems were incubated for 2 days on co-culture medium (1/10 MS salts, 3% sucrose, pH 5.7) containing 6 g/L agar at 22° C. in a Percival growth chamber (16 hrs light) and subsequently transferred to callus induction medium (CIM, MS medium supplemented with 3% sucrose 3, 2.5 mg/L of zeatin riboside, 0.1 mg/L of naphthalene acetic acid, and 6 g/L of agar) containing timentine (150 mg/L) and kanamycin (100 mg/L). After 1 month of culture on CIM, explants were transferred to shoot induction medium (SIM, MS medium supplemented with 3% sucrose, 2.5 mg/L of zeatin riboside, 0.3 mg/L of giberelic acid GA3, and 6 g/L of agar) containing timentine and kanamycin (150 and 100 mg/L respectively). After 3-4 weeks, the number of explants developing transgenic calli and/or shoots was counted. More calli were observed on potato stem explants infected with an *Agrobacterium* strain containing the P-DNA vector (0.59 calli/explant) than on explants infected with the control T-DNA vector pBI121 (Genbank accession number AF85783) (0.31 calli/explant).

Turf seedlings were also infected with a modified P-DNA vector comprising a ubiquitin-4 promoter driving GUS expression. GUS assays on the transformed plants showed that transformation efficiency were similar to those with control T-DNA vectors.

2. Cytokinin Genes as Backbone-Integration Markers

To make it possible to select against the frequent occurrence of backbone integration events, an expression cassette comprising the *Agrobacterium* isopentenyl transferase (IPT) gene driven by the Ubi3 promoter and followed by the Ubi3 terminator (SEQ ID NO.: 3) was inserted as 2.6 kbp SacII fragment into the backbone of the P-DNA vector described above.

Transformed shoots, generated by infecting potato leaf explants as described above, could be grouped into two different classes. The first class of shoots (55 of 193) was phenotypically indistinguishable from control shoots transformed with LBA::pBI121. The second class of shoots (138 of 193) displayed an IPT phenotype. Shoots of the latter class were stunted in growth, contained only very small leaves, displayed a light-green to yellow color, and were unable to root upon transfer to hormone-free media. To confirm that shoots with an IPT phenotype contained the IPT gene stably integrated in their genomes, all shoots were transferred to Magenta boxes containing MS medium supplemented with 3% sucrose and timentine 150 mg/L, allowed to grow for 3 to 4 additional weeks, and used to isolate DNA. This plant DNA served as template in PCR reactions with an oligonucleotide pair designed to anneal to the IPT gene: 5'-GTC CAA CTT GCA CAG GAA AGA C-3' (SEQ ID NO: 25), and 5'-CAT GGA TGA AAT ACT CCT GAG C-3' (SEQ ID NO: 26). This PCR experiment confirmed a strict correlation between IPT phenotype and presence of the IPT gene. A second PCR experiment was carried out to test whether IPT-free plants did not contain any other backbone sequences. Because the IPT expression cassette is positioned close to the left border-like sequences, the oligonucleotide pair for this experiment was designed to anneal to backbone sequences close to the right border-like sequence: 5'-CAC GCT AAG TGC CGG CCG TCC GAG-3' (SEQ ID NO: 27), and 5'-TCC TAA TCG ACG GCG CAC CGG CTG-3' (SEQ ID NO: 28). Data from this experiment confirm that plants that are positive for the IPT gene are also positive for this other part of the backbone.

3. New Terminators

Instead of the frequently used bacterial terminator of the nopaline synthase gene, a new sequence derived from a food source was used to terminate transcription of a selectable marker gene. This terminator is the yeast alcohol dehydrogenase-1 (ADH1) terminator (Genbank accession number V01292, SEQ ID NO. 4). Surprisingly, this specific yeast terminator was shown to function effectively in plant cells by Agro-infecting potato stem explants with different binary vectors that carry an intron-containing GUS gene operably linked to the Ubi7 promoter and followed by either that terminator or the yeast CYC1 terminator. Five days after infection, high levels of transient GUS expression were monitored with the ADH1 terminator, whereas almost no GUS expression was detected with the CYC1 terminator. To terminate transcription of a desired polynucleotide in dicotyledonous plant species, the potato Ubiquitin-3 terminator was used (SEQ ID NO.:5). For transcriptional termination in monocotyledonous plant species, a new terminator was amplified from DNA of the rice variety "Lemont", where it is associated with the actin-1 gene, with the primer set: 5'-GGATCCTCGTCATTTACTTTTATCTTAATGAGC-3' (SEQ ID NO: 29) and 5'-GAATTCACATTATAAGCTTTATATTACCAAGG-3' (SEQ ID NO.:38). Functional activity of this rice terminator was demonstrated by operably linking it to a promoter-GUS fusion. Five days after infecting bentgrass seedlings with an *Agrobacterium* strain containing the resulting expression cassette between borders of a binary vector, transient GUS expression levels were equally high as with a control experiment based on a similar vector carrying the frequently used terminator of the bacterial nopaline synthase gene.

4. New Promoters

Instead of viral promoters such as the 35S promoter of cauliflower mosaic virus, new plant promoters were developed and used to express genes in transgenic plants. For some important dicotyledonous plants including potato and cotton, a new promoter was isolated from the potato genome. This new promoter represents a small part (492-bp) of the previously described 1220-bp and 1788-bp promoters of the potato Ubiquitin-7 gene (Garbarino et al., U.S. Pat. No. 6,448,391 B1, 2002). This conveniently-sized fragment (SEQ ID NO.: 7) was tested for its efficacy to promote high-level expression of transgenes by Agro-infecting tobacco explants with a binary vector carrying the fragment operably linked to the NPTII gene, and placing the infected explants on MS media containing 100 mg/L kanamycin. Within two weeks, a large number of calli developed on these explants, whereas explants infected with a control strain did not contain any calli. Apart from tobacco, the small new promoter was also shown to be active in potato and cotton. An alternative promoter that can be used to drive high-level expression represents 1,026-bp of the Ubi7 promoter (SEQ ID NO.: 8).

For monocotyledonous plants, a promoter was developed that resembles the sugarcane ubiquitin-4 promoter. The sequence of this small promoter, designated UbiN, is shown in SEQ ID NO.:9; its homology with the corresponding part of the original Ubiquitin-4 promoter is shown in FIG. 3. The functional activity of UbiN was assessed by first inserting it between a small HindIII-SalI 0.2-kbp DNA fragment (SEQ ID NO.: 10) isolated from a modified maize matrix attachment region using the primer set: 5'-AAG CTT AAT AGC TTC ACC TAT ATA ATA-3' (SEQ ID NO: 30), and 5'-GTC GAO GGC GTT TAA CAG GCT-3' (SEQ ID NO: 31), and a modified EcoRI-BamHI 1.4-kbp fragment containing an intron associated with a sugarcane ubiquitin gene, using the primer set 5'-GAA TTC CCT TCG TCG GAG AAA TTC ATC GAA G-3' (SEQ ID NO: 32), and 5'-GGA TCC CTG CAA GCA TTG AGG ACC AG-3' (SEQ ID NO.: 39). The fused DNA fragments were then operably linked to the CAH gene followed by a terminator, and a binary vector containing this expression cassette was used to Agro-infect bentgrass seedlings as described in Example 1. Vigorously growing calli demonstrated that the sugarcane-derived promoter is effective in promoting transgene expression.

5. New Vectors

As shown in FIG. 1, a vector of the present invention may comprise, in 5'- to 3'-orientation, (i) a cytokinin gene (the backbone integration marker) operably linked to elements that can express it, (ii) a first border(-like) P-DNA sequence, (iii) a desired polynucleotide that is operably linked to a promoter and terminator, (iv) an optional selectable marker that is operably linked to a promoter and a terminator, which is associated with a gene that is not naturally expressed in plants, and (v) a second border(-like) P-DNA sequence. A vector also may comprise another desired polynucleotide operably linked to a promoter and terminator, preferably derived from food sources, and inserted within the T-DNA or P-DNA sequence.

TABLES

TABLE 2

*Arabidopsis* transformation in T0

| Experiment | Transgene | Treatment | GUS-positive seedlings |
|---|---|---|---|
| 85-6 | GUS | 5-min. vortex | 15% (11 of 74) |
| 90-1 | GUS | 5-min. vortex | 21% (16 of 75) |
| 95-1 | GUS | 5-min. vortex | 17% (30 of 181) |
| 91-1 | GUS | 5-min. vortex | 5% (3 of 62) |
| 92-1 | GUS | 5-min. vortex | 18% (15 of 183) |
| 90-3 | GUS | 5-min. vortex | 16% (14 of 87) |
| AVERAGE | GUS | 5-min. vortex | 13% (89 of 662) |
| 85-5 | GUS | 30-min. vortex | 15% (11 of 74) |
| 90-2 | GUS | 30-min. vortex | 7% (5 of 69) |
| 91-2 | GUS | 30-min. vortex | 9% (4 of 47) |
| 91-4 | GUS | 30-min. vortex | 3% (2 of 80) |
| 90-4 | GUS | 30-min. vortex | 1% (1 of 72) |
| 92-4 | GUS | 30-min. vortex | 11% (14/123) |
| 63-2 | GUS | 30-min. vortex | 32% (27/84) |
| 63-3 | GUS | 30-min. vortex | 24% (15/63) |
| AVERAGE | GUS | 30-min. vortex | 13% (79 of 612) |

TABLE 3

Transgenic *Arabidopsis* plants in selfed progeny

| Experiment | Transgene | GUS-positive seedlings |
|---|---|---|
| 63-2-67 | GUS | 37% (43 of 117) |
| 63-6-16 | GUS | 51% (55 of 108) |
| 63-3-57 | GUS | 71% (36 of 51) |
| 63-3-60 | GUS | 64% (54 of 85) |
| 78-8-34 | GUS | 56% (53 of 94) |
| 63-2-22 | GUS | 48% (73 of 153) |
| 63-3-12 | GUS | 48% (70 of 147) |
| 69-2-60 | GUS | 78% (53 of 68) |
| AVERAGE | GUS | 53% (437 of 823) |

TABLE 4

Tobacco transformation in T0

| Experiment | Transgene | Treatment | GUS-positive seedlings |
|---|---|---|---|
| 94-1 | GUS | 5-min. vortex | 4% (4 of 94) |
| 91-5 | GUS | 5-min. vortex | 0% (0 of 74) |
| 94-2 | GUS | 5-min. vortex | 7% (7 of 100) |
| 91-6 | GUS | 5-min. vortex | 1% (1 of 75) |
| 75-1 | GUS | 5-min. vortex | 8% (15 of 194) |
| 78-5 | GUS | 5-min. vortex | 19% (17 of 91) |
| AVERAGE | GUS | 5-min. vortex | 7% (44 of 628) |
| 85-2 | GUS | 30-min. vortex | 0% (0 of 23) |
| 92-6 | GUS | 30-min. vortex | 0% (0 of 127) |
| 73-2 | GUS | 30-min. vortex | 10% (16 of 155) |
| 73-1 | GUS | 30-min. vortex | 5% (7 of 135) |
| 70-3 | GUS | 30-min. vortex | 8% (4 of 51) |
| 68-3 | GUS | 30-min. vortex | 0% (0 of 49) |
| 60-1 | GUS | 30-min. vortex | 2% (2 of 83) |
| 68-1 | GUS | 30-min. vortex | 8% (5 of 61) |
| 80-1 | GUS | 30-min. vortex | 2% (2 of 97) |
| 80-3 | GUS | 30-min. vortex | 7% (4 of 54) |

TABLE 4-continued

Tobacco transformation in T0

| Experiment | Transgene | Treatment | GUS-positive seedlings |
|---|---|---|---|
| 85-1 | GUS | 30-min. vortex | 4% (1 of 27) |
| AVERAGE | GUS | 30-min. vortex | 5% (41 of 862) |

TABLE 5

Transgenic tobacco plants in selfed progeny

| Experiment | Transgene | GUS-positive seedlings |
|---|---|---|
| 62-3-11 | GUS | 12% (10 of 85) |
| 70-3-18 | GUS | 15% (16 of 110) |
| 70-3-23 | GUS | 27% (74 of 275) |
| 70-4-49 | GUS | 22% (20 of 91) |
| AVERAGE | GUS | 21% (120 of 561) |

TABLE 6

Transgenic creeping bentgrass in selfed progeny

| Experiment | Transgene | Treatment in T0 | CAH-positive seedlings |
|---|---|---|---|
| 5G-23 | CAH | Dormex screen | 4 of 21 |
| 3B-7 | CAH | Dormex screen | 1 of 3 |
| 3B-14 | CAH | Dormex screen | 0 of 1 |
| AVERAGE | CAH | Dormex screen | 20% (5 of 25) |
| 5J-18 | CAH | Cyanamide selection | 1 of 1 |
| 5J-23 | CAH | Cyanamide selection | 4 of 5 |
| AVERAGE | CAH | Cyanamide selection | ~83% (5 of 6) |

SEQ ID NOs.
SEQ ID NO.:1 Cyanamide tolerance gene from *Aspergillus* sp.
SEQ ID NO.:2 Potato P-DNA. The bold underlined portions represent the left (5'-) and right (3'-) border-like sequences of the P-DNA respectively.
SEQ ID NO.:3 Expression cassette for the cytokinin IPT gene
SEQ ID NO.:4 Terminator associated with the yeast ADH1 gene
SEQ ID NO.:5 Terminator associated with the potato Ubiquitin-3 gene
SEQ ID NO.:6 Terminator associated with the rice actin-1 gene
SEQ ID NO.:7 Short 0.5-kbp promoter associated with the potato Ubiquitin-7 gene
SEQ ID NO.:8 Short 1.0-kbp promoter associated with the potato Ubiquitin-7 gene
SEQ ID NO.:9 Plant-like promoter
SEQ ID NO.:10 Part of a maize matrix-associated region
SEQ ID NO.:11 Intron associated with the sugarcane Ubiquitin-4 gene SEQ ID No. 1
ATGTGTCAGAACGAAGTTGAAGTCAATGGCTGGACCAGCATGCCTGCTGA
TGCTGGCGCCATCTTTGATGGTGGACCCTTCATCAACGTACCGGAAGCCC
TGTCGATCGAAGAGATCAAGTTTCCAGTCGATGACCCCATTGTTGAGAAA
ACCATGAGATATGCAAAGGCTGCTCTTCCCACTGAAACATTCAACCACTC
TATGAGAGTTTACTATTACGGTATGCAGGACTGCGCTTCCCATGGTGTCT
TAATCAATCGCTCACAGGCTCTAGGAATGGCTATCACCAAGCAGCAATTC
CCGAAGCAAGCCAGTGCCCTTAGCCCCAGTACCTGGGCCTTGACCTGTTT
GCTGCACGACATCGGTACTTCCGACCACAACCTCGCTGCAACTCGCATGT
CCTTTGATATCTACGGTGGTATCAAGGCTCTGGAGGTTCTTAAGGGGTTT
GGCGCTACCTCCGATCAGGCCGAAGCGGTCGCTGAGGCCATCATCCGACA
CCAGGATCTCGGAGTTCATGGGACGATCACGTATATCGGCCAGCTCATCC
AGCTGGCCACCATCTACGATAACGTCGGGGCTCACCCTTACGTCAAAGAC TTTGGCGAGTTGATCCATGATACAACTCGCTCCCAGGTGCACGAGGCGCA
CCCGCCGGGGAATGGCGCACGTTCTTCTCTGGCGTCATCCAGAAGGAGC
AAGCAATCAAGCCCTGGTGTCATACAAAAAAGATGGTGAATGTTCTGAGG
AAAGGAAGCCGGCACCCTGATGGGCAGTGA SEQ ID No. 2
GTTTACATTACCATATATCCTGTCAGAGGTATAGAGGCATGACTGGCATG
ATCACTAAATTGATGCCCACAGAGGAGACTTATAACCTACAGGGGCACGT
AGTTCTAGGACTTGAAAGTGACTGACCGTAGTCCAACTCGGTATAAAGCC
TACTCCCAACTAAATATATGAAATTTATAGCATAACTGCAGATGAGCTCG
ATTCTAGAGTAGGTACCGAGCTCGAATTCCTTACTCCTCCACAAAGCCGT
AACTGAAGCGACTTCTATTTTTCTCAACCTTCGGACCTGACGATCAAGAA
TCTCAATAGGTAGTTCTTCATAAGTGAGACTATCCTTCATAGCTACACTT
TCTAAAGGTACGATAGATTTTGGATCAACCACACACACTTCGTTTACATC
GGTATATATCCTGCCA

SEQ ID No. 3
CTGCAGCCAAAGCACATACTTATCGATTTAAATTTCATCGAAGAGATTAA
TATCGAATAATCATATACATACTTTAAATACATAACAAATTTTAAATACA
TATATCTGGTATATAATTAATTTTTTAAAGTCATGAAGTATGTATCAAAT
ACACATATGGAAAAAATTAACTATTCATAATTTAAAAAAATAGAAAAGATA
CATCTAGTGAAATTAGGTGCATGTATCAAATACATTAGGAAAAGGGCATA
TATCTTGATCTAGATAATTAACGATTTTGATTTATGTATAATTTCCAAAT
GAAGGTTTATATCTACTTCAGAAATAACAATATACTTTTATCAGAACATT
CAACAAAGTAACAACCAACTAGAGTGAAAAATACACATTGTTCTCTAAAC
ATACAAAATTGAGAAAAGAATCTCAAAATTTAGAGAAACAAATCTGAATT
TCTAGAAGAAAAAAATAATTATGCACTTTGCTATTGCTCGAAAAATAAAT
GAAAGAAATTAGACTTTTTTAAAAGATGTTAGACTAGATATACTCAAAAG
CTATCAAAGGAGTAATATTCTTCTTACATTAAGTATTTTAGTTACAGTCC
TGTAATTAAAGACACATTTTAGATTGTATCTAAACTTAAATGTATCTAGA
ATACATATATTTGAATGCATCATATACATGTATCCGACACACCAATTCTC
ATAAAAAGCGTAATATCCTAAACTAATTTATCCTTCAAGTCAACTTAAGC
CCAATATACATTTTCATCTCTAAAGGCCCAAGTGGCACAAAATGTCAGGC
CCAATTACGAAGAAAAGGGCTTGTAAAACCCTAATAAAGTGGCACTGGCA
GAGCTTACACTCTCATTCCATCAACAAAGAAACCCTAAAAGCCGCAGCGC
CACTGATTTCTCTCCTCCAGGCGAAGATGCAGATCTTCGTGAAGACCCTA
ACGGGGAAGACGATCACCCTAGAGGTTGAGTCTTCCGACACCATCGACAA
TGTCAAAGCCAAGATCCAGGACAAGGAAGGGATTCCCCCAGACCAGCAGC
GTTTGATTTTCGCCGGAAAGCAGCTTGAGGATGGTCGTACTCTTGCCGAC
TACAACATCCAGAAGGAGTCAACTCTCCATCTCGTGCTCCGTCTCCGTGG
TGGTGGATCCATGGACCTGCATCTAATTTTCGGTCCAACTTGCACAGGAA
AGACGACGACCGCGATAGCTCTTGCCCAGCAGACAGGGCTTCCAGTCCTT
TCGCTTGATCGGGTCCAATGCTGTCCTCAACTATCAACCGGAAGCGGACG
ACCAACAGTGGAAGAACTGAAAGGAACGACGCGTCTCTACCTTGATGATC
GGCCTCTGGTGGAGGGTATCATCGCAGCCAAGCAAGCTCATCATAGGCTG
ATCGAGGAGGTGTATAATCATGAGGCCAACGGCGGGCTTATTCTTGAGGG
AGGATCCACCTCGTTGCTCAACTGCATGGCGCGAAACAGCTATTGGAGTG
CAGATTTTCGTTGGCATATTATTCGCCACAAGTTACCCGACCAAGAGACC
TTCATGAAAGCGGCCAAGGCCAGAGTTAAGCAGATGTTGCACCCCGCTGC
AGGCCATTCTATTATTCAAGAGTTGGTTTATCTTTGGAATGAACCTCGGC
TGAGGCCCATTCTGAAAGAGATCGATGAGATATCGATATGCCATGTTGTTT
GCTAGCCAGAACCAGATCACGGCAGATATGCTATTGCAGCTTGACGCAAA
TATGGAAGGTAAGTTGATTAATGGGATCGCTCAGGAGTATTTCATCCATG
CGCGCCAACAGGAACAGAAATTCCCCCAAGTTAACGCAGCCGCTTTCGAC
GGATTCGAAGGTCATCCGTTCGGAATGTATTAGGTTACGCCAGCCCTGG
TCGCACCTGTCTTCATCTGGATAAGATGTTCGTAATTGTTTTTGGCTTTG
TCCTGTTGTGGCAGGGCGGCAAATACTTCCGACAATCCATCGTGTCTTCA
AACTTTATGCTGGTGAACAAGTCTTAGTTTCCACGAAAGTATTATGTTAA
ATTTTAAAATTTCGATGTATAATGTGGCTATAATTGTAAAAATAAACTAT
CGTAAGTGTGCGTGTTATGTATAATTTGTCTAAATGTTTAATATATATCA
TAGAACGCAATAAATATTAAATATAGCGCTTTTATGAAATATAAATACAT
CATTACAAGTTGTTTATATTTCGGGTGGACTAGTTTTAATGTTTAGCAA
ATGTCCTATCAGTTTTCTCTTTTTGTCGAACGGTAATTTAGAGTTTTTTT
TGCTATATGGATTTTCGTTTTTGATGTATGTGACAACCCTCGGGATTGTT
GATTTATTTCAAAACTAAGAGTTTTTGCTTATTGTTCTCGTCTATTTTGG
ATATCAATCTTAGTTTTATATCTTTTCTAGTTCTCTACGTGTTAAATGTT
CAACACACTAGCAATTTGGCTGCAGCGTATGGATTATGGAACTATCAAGT
CTGTGGGATCGATAAATATGCTTCTCAGGAATTTGAGTTTTACAGTCTT
TATGCTCATTGGGTTGAGTATAATATAGTAAAAAAATAGGAATTC

SEQ ID No. 4
TTCTTCGCCAGAGGGTTTGGTCAAGTCTCCAATCAAGGTTGTCGGCTTGTC
TACCTTGCCAGAAATTTACGAAAAGATGGAAAAGGGTCAAATCGTTGGTA
GATACGTTGTTGACACTTCTAAATAAGCGAATTTCTTATGATTTATGATT
TTTATTATTAAATAAGTTATAAAAAAAATAAGTGTATACAAATTTTAAAG
TGACTCTTAGGTTTTAAAACGAAAATTCTTATTCTTGAGTAACTCTTTCC
TGTAGGTCAGGTTGCTTTCTCAGGTATAGCATGAGGTCGCTC

SEQ ID No. 5
TTGATTTTAATGTTTAGCAAATGTCCTATCAGTTTTCTCTTTTTGTCGAA
CGGTAATTTAGAGTTTTTTTTGCTATATGGATTTTCGTTTTTGATGTATG

-continued

TGACAACCCTCGGGATTGTTGATTTATTTCAAAACTAAGAGTTTTTGCTT
ATTGTTCTCGTCTATTTTGGATATCAATCTTAGTTTTATATCTTTTCTAG
TTCTCTACGTGTTAAATGTTCAACACACTAGCAATTTGGCTGCAGCGTAT
GGATTATGGAACTATCAAGTCTGTGGGATCGATAAATATGCTTCTCAGGA
ATTTGAGATTTTACAGTCTTTATGCTCATTGGGTTGAGTATAATATAGTA
AAAAAATAG

SEQ ID No. 6

AGTATTTTCGCATGAATGTTCTTTTCTTCTGTCTTGTGTGCATCAGTGATCT
AGTGCATGGGAGTTTGTATTGTGATGTTCGACATCACGTAACTTCCACTT
TGCCTTTGCTGTTCGATATTTTAATGACATGTCACACACACTTCTGATAC
TTTTCTTTCTTGGCTATTGTGCCAGCATGATGCAAGATGCATCACAGCAT
CAGATATATTCTCATCGTCAGGCTTTAGCAGCACACAGAGCACGCTTTGCC
GCTTAAAAGTTGTACGGCGCAGCTTAGACATCCCCTGTAGAAGTGATAAT
CTTTTCACTTTTCCTTAAACAAATTGAGAGGGGAAATGGAACCATGTGGA
TCAGAGAAGCTTTTGTTTCTTTACACAAGAATATTTGGTACAGTGGGGGT
CCTATGTTCGTGGGTTCGTGGCTTGGCTGCCTGTCTTCAACCAAGTGTTT
TCAGTTCAACATGTTAGCGTGTAGAAAGAGCACAATTCTGTTTATCTCCA
AGGTAAAATGTGGCATTCTGTTAAAGAACATGATCCTGCCAATTTTTTAA
GTTTCAATGGAAGAGGAATGTAAAGCTTTCTATGGTTTGTGTACACAACA
CAGTGGAAGAGGAGTGCAAGCTTTCT

SEQ ID No. 7

AAATAACAAATATCAATATGAGGTCAATAACAATATCAAAATAATATGAA
AAAAGAGCAATACATAATATAAGAAAGAAGATTTAAGTGCGATTATCAAG
GTAGTATTATATCCTAATTTGCTAATTCTTATATTTAAGGTC
ATGTTCATGATAAACTTGAAATGCGCTATATTAGAGCATATATTAAAATA
AAAAAATACCTAAAATAAAATTAAGTTATTTTTAGTATATATTTTTTTAC
ATGACCTACATTTTTCTGGGTTTTCTAAAGGAGCGTGTAAGTGTCGACC
TCATTCTCCTAATTTTCCCCACCACATAAAAATTAAAAAGGAAAGGTAGC
TTTTGCGTGTTGTTTTGGTACACTACACCTCATTATTACACGTGTCCTCA
TATAATTGGTTAACCCTATGAGGCGGTTTCGTCTAGAGTCGGCCATGCCA
TCTATAAAATGAAGCTTTCTGCACCTCATTTTTTTCATCTTC

SEQ ID No. 8

TAATATTTACATTAGTTTTGTTGATGAGGATGACAAGATTTTGGTCATCA
ATTACATATACCCAAATTGAATAGTAAGCAACTTAATGTTTTTCATAATG
ATAATGACGACACAAAAAAAAACCCATTTATTATTCACATTGATTGAGTT
TTATATGCAATATAGTAATAATAATTTCTTATAAAGCAAGAGGTC
AATTTTTTTTAATTATACCAACGTCACTAAATTATATTTGATAATGTAA
AACAATTCAATTTTACTTAAATATCATGAAATAAACTATTTTTATAACCA
AATTACTAAATTTTTCCAATAAAAAAAAGTCATTAAGAAGACATAAAATA
AATTTGAGTAAAAGAGTGAAGTCGACTGACTTTTTTTTTTTTTATCATA
AGAAAATAAATTATTAACTTTAACCTAATAAAACACTAATATAATTTCAT
GGAATCTAATACTTACCTCTTAGAAATAAGAAAAGTGTTTCTAATAGAC
CCTCAATTTACATTAAATATTTTCAATCAAATTTAAATAACAAATATCAA
TATGAGGTCAATAACAATATCAAAATAATATGAAAAAAGAGCAATACATA
ATATAAGAAAGAAGATTTAAGTGCGATTATCAAGGTAGTATTATATCCTA
ATTTGCTAATATTTAAACTCTTATATTTAAGGTCATGTTCATGATAACT
TGAAATGCGCTATATTAGAGCATATATTAAAATAAAAAAATACCTAAAAT
AAAATTAAGTTATTTTTAGTATATATTTTTTTACATGACCTACATTTTTC
TGGGTTTTCTAAAGGAGCGTGTAAGTGTCGACCTCATTCTCCTAATTTT

-continued

CCCCACCACATAAAAATTAAAAAGGAAAGGTAGCTTTTGCGTGTTGTTTT
GGTACACTACACCTCATTATTACACGTGTCCTCATATAATTGGTTAACCC
TATGAGGCGGTTTCGTCTAGAGTCGGCCATGCCATCTATAAAATGAAGCT
TTCTGCACCTCATTTTTTTCATCTTC

SEQ ID No. 9

GTCGACAAGCAAAGGGTATGGCAACTGTGTCACCGCCCTTCGCTGCGTGT
TAACGGCCACCAACCGCAGGTAGCAAACGGCGTGCACCTTCCCGAGATCT
CCACAGCGAGGTCTGGCTTTTTCCGCCTTCCCGGAAACCGCGGTGGTTTC
AGCGTGGCGGATTCCCCCTCCCACCACCCAACCGCCATAAATACCAGCCC
CCACCTCACTCTCTTTGCATATCCATCCAAATCCCAGTCCCCAATCGAAT
TCC

SEQ ID No. 10

AAGCTTAATAGCTTCACCTATATAATACTTCATCCATTTTATTAGTACAT
CCATTTAGGGTTTAGGGTTAATGGTTTTTATAGACTAATTTTTTTAGTAC
ATCTATTTTATTCTATTTTAGCCTCTAAATTAAGAAAACTAAAACTCTAT
TTTAGTTTTTTTATTTAATAATTTAGATATAAAATAGAATAAAATAAAGT
GACTAAAAATTAAACAAATACCCTTTAAGAAATTAAAAAAAACTAAGGAAA
CATTTTTCTTGTTTCGAGTAGATAATGCCAGCCTGTTAAACGCCGTCGAC

SEQ ID No. 11

GAATTCCCTTCGTCGGAGAAATTCATCGAAGCGAAGCGAATCCTCGCGAT
CCTCTCAAGGTACTGCGAGTTTTCGATCCCCCTCTCGACCCCTCGTATGT
TTGTGTTTGTCGTACGTTTGATTAGGTATGCTTTCCCTGTTTGTGTTCGT
CGTAGCGTTTGATTAGGTATGCTTTCCCTGTTCGTGTTCATCGTAGTGTT
TGATTAGGTCGTGTGAGGCGATGGCCTGCTCGCGTCCTCGATCTGTAGT
CGATTTGCGGGTCGTGGTGTAGATCGCGGGCTGTGATGAAGTTATTTGG
TGTGATCTGCTCGCCTGATTCGCGGGTTGGCTCGAGTAGATATGGATGG
TTGGACCGGTTGGTTCGTTTACCGCGCTAGGGTTGGGCTGGGATGATGT
GCATGCGCCGTTGCGCGTGATCCCGCAGCAGGACTTGCGTTTGATTGCCA
GATCTCGTTACGATTATGTGATTTGGTTTGGACTTATTAGATCTGTAGCT
TCTGCTTATGTTGCCAGATGCGCCTACTGCTCCATATGCCTGATGATAAT
CCATAAATGGCAGTGGAAATCAACTAGTTGATTGCGGAGTCATGTATCAG
CTACAGGTGTAGGGACTAGCTACAGGTGTAGGGACTGCGTCTAATTGTTT
GGTCCTTAACTCATGTGCAATTATGCAATTTAGTTTAGATGTTTGTTCCA
ATCATCTAGGCTGTAAAAGGGACACTGGTTAGATTGCTGTTTAATCTTTT
TAGTAGATTATATTATATTGGTAACTTATTAACCCTATTACATGCCATAA
CGTGGATTCTGCTCATGCCTGATGATAATCATAGATCACTGTGGAATTAA
TTAGTTGATTGTTGAATCATGTTTCATGTACATACCACGGCACAATTGCT
TAGTTCCTTAACAAATGCAAATTTTACTGATCCATGTATGATTTGCGTGG
TTCTCTAATGTGAAATACTATAGCTACTTGTTAGTAAGAATCAGGTTCGT
ATGCTTAATGCTGTATGTGCCTTCTGCTCATGCCTGATGATAATCATATA
TCACTGGAATTAATTAGTTGATCGTTTAATCATATATCAAGTACATACCA
TGGCACAATTTTAGTCACTTAACCCATGCAGATTGAACTGGTCCCTGCA
TGTTTTGCTAAATTGTTCTATTCTGATTAGACCATATATCAGGTATTTTT
TTTTGGTAATGGTTCTCTTATTTAAATGCTATATAGTTCTGGTACTTGT
TAGAAAGATCTGGTTCATAGTTTAGTTGCCTATCCTTCGAATTAGGATGC
TGAGCAGCTGATCCTATAGCTTTGTTTCATGTATCAATTCTTTTGTGTTC
AACAGTCAGTTTTTGTTAGATTCATTGTAACTTATGTTCGCTTACTCTTC
TGGTCCTCAATGCTTGCAGGGATCC

What is claimed is:

1. A method for producing a transgenic plant, comprising:
   (a) vortexing a solution comprising a germinating plant seedling, and at least one *Agrobacterium* strain that harbors a plasmid vector carrying a desired polynucleotide;
   (b) cultivating said *Agrobacterium*-transformed seedling in or on tissue culture medium;
   (c) producing a callus from said transformed seedling, and inducing shoot and root formation from said callus to produce a plantlet;
   (d) transferring said transformed plantlet to soil, and exposing said transformed plantlet to conditions that promote growth into a plant; and
   (e) screening said plant to determine if said desired polynucleotide is integrated into the genome of at least one cell of said plant, wherein said plant is stably transformed;
   wherein the vector comprises a T-DNA or P-DNA that comprises (i) the desired polynucleotide and (ii) a selectable marker gene operably linked to a terminator that is not naturally expressed in plants.

2. The method of claim 1, wherein said vector further comprises a backbone integration marker gene that is not positioned within the T-DNA or within the P-DNA.

3. The method of claim 1, wherein the step of producing a callus from said transformed seedling comprises:
   (i) transferring said transformed seedling to tissue culture medium that contains auxin and cyanamide, to produce calli;
   (ii) selecting fertilizer-tolerant calli;
   (iii) inducing shoot and root formation from said selected calli to produce plantlets; and
   (iv) transferring said plantlets to soil, and exposing said plantlets to conditions that promote growth of said transgenic plants from said plantlets.

4. A method for producing a transgenic plant, comprising:
   (a) vortexing a solution comprising a germinating plant seedling and at least one *Agrobacterium* strain that harbors a plasmid vector carrying a desired polynucleotide;
   (b) cultivating said *Agrobacterium*-transformed seedling in or on tissue culture medium;
   (c) producing a callus from said transformed seedling by (i) transferring said transformed seedling to tissue culture medium that contains auxin and cyanamide, and (ii) selecting fertilizer-tolerant calli;
   (d) inducing shoot and root formation from said selected calli to produce plantlets;
   (e) transferring said plantlets to soil, and exposing said transformed plantlets to conditions that promote growth into a plant; and
   (f) screening said plant to determine if said desired polynucleotide is integrated into the genome of at least one cell of a plant, wherein said plant is stably transformed;
   wherein the vector comprises (a) a T-DNA or P-DNA that comprises (i) the desired polynucleotide, and (ii) a selectable marker gene operably linked to a terminator that is not naturally expressed in plants; and wherein said vector optionally further comprises (b) a backbone integration marker gene that is not positioned within the T-DNA or within the P-DNA.

\* \* \* \* \*

SEQUENCE LISTING

<160> NUMBER OF SEQ ID NOS: 39

<210> SEQ ID NO 1
<211> LENGTH: 780
<212> TYPE: DNA
<213> ORGANISM: Aspergillus sp.

<400> SEQUENCE: 1
atgtgtcaga acgaagttga agtcaatggc tggaccagca tgcctgctga tgctggcgcc    60
atctttgatg gtggacccctt catcaacgta ccggaagccc tgtcgatcga agagatcaag   120
tttccagtcg atgaccccat tgttgagaaa accatgagat atgcaaaggc tgctcttccc   180
actgaaacat tcaaccactc tatgagagtt tactattacg gtatgcagga ctgcgcttcc   240
catggtgtct taatcaatcg ctcacaggct ctaggaatgg ctatcaccaa gcagcaattc   300
ccgaagcaag ccagtgccct tagccccagt acctgggcct tgacctgttt gctgcacgac   360

```
atcggtactt ccgaccacaa cctcgctgca actcgcatgt cctttgatat ctacggtggt        420
atcaaggctc tggaggttct taaggggttt ggcgctacct ccgatcaggc cgaagcggtc        480
gctgaggcca tcatccgaca ccaggatctc ggagttcatg ggacgatcac gtatatcggc        540
cagctcatcc agctggccac catctacgat aacgtcgggg ctcacccttta cgtcaaagac      600 tttggcgagt tgatccatga tacaactcgc tcccaggtgc acgaggcgca cccgccgggg       660
gaatggcgca cgttcttctc tggcgtcatc cagaaggagc aagcaatcaa gccctggtgt       720
catacaaaaa agatggtgaa tgttctgagg aaggaagcc ggcaccctga tgggcagtga        780

<210> SEQ ID NO 2
<211> LENGTH: 416
<212> TYPE: DNA
<213> ORGANISM: Solanum tuberosum

<400> SEQUENCE: 2
gtttacatta ccatatatcc tgtcagaggt atagaggcat gactggcatg atcactaaat        60
tgatgcccac agaggagact tataacctac aggggcacgt agttctagga cttgaaagtg       120
actgaccgta gtccaactcg gtataaagcc tactcccaac taaatatatg aaatttatag       180
cataactgca gatgagctcg attctagagt aggtaccgag ctcgaattcc ttactcctcc       240
acaaagccgt aactgaagcg acttctattt ttctcaacct tcggacctga cgatcaagaa       300
tctcaatagg tagttcttca taagtgagac tatccttcat agctacactt tctaaaggta      360
cgatagattt tggatcaacc acacacactt cgtttacatc ggtatatatc ctgcca          416

<210> SEQ ID NO 3
<211> LENGTH: 2595
<212> TYPE: DNA
<213> ORGANISM: Artificial Sequence
<220> FEATURE:
<223> OTHER INFORMATION: Description of Artificial Sequence: Cytokinin
      IPT gene plasmid

<400> SEQUENCE: 3
ctgcagccaa agcacatact tatcgattta aatttcatcg aagagattaa tatcgaataa        60
tcatatacat actttaaata cataacaaat tttaaataca tatatctggt atataattaa       120
ttttttaaag tcatgaagta tgtatcaaat acacatatgg aaaaaattaa ctattcataa       180
tttaaaaaat agaaaagata catctagtga aattaggtgc atgtatcaaa tacattagga       240
aaagggcata tatcttgatc tagataatta acgattttga tttatgtata atttccaaat       300
gaaggtttat atctacttca gaaataacaa tatactttta tcagaacatt caacaaagta       360
acaaccaact agagtgaaaa atacacattg ttctctaaac atacaaaatt gagaaaagaa       420
tctcaaaatt tagagaaaca aatctgaatt tctagaagaa aaaataatt atgcactttg        480 ctattgctcg aaaaataaat gaaagaaatt agacttttt aaaagatgtt agactagata       540
tactcaaaag ctatcaaagg agtaatattc ttcttacatt aagtattta gttacagtcc       600 tgtaattaaa gacacatttt agattgtatc taaacttaaa tgtatctaga atacatatat      660
ttgaatgcat catatacatg tatccgacac accaattctc ataaaaagcg taatatccta      720
aactaattta tccttcaagt caacttaagc ccaatataca ttttcatctc taaaggccca      780
agtggcacaa aatgtcaggc ccaattacga agaaaagggc ttgtaaaacc ctaataaagt      840
ggcactggca gagcttacac tctcattcca tcaacaaaga aaccctaaaa gccgcagcgc      900
cactgatttc tctcctccag gcgaagatgc agatcttcgt gaagacccta acggggaaga      960
cgatcaccct agaggttgag tcttccgaca ccatcgacaa tgtcaaagcc aagatccagg     1020
```

```
acaaggaagg gattcccca gaccagcagc gtttgatttt cgccggaaag cagcttgagg    1080
atggtcgtac tcttgccgac tacaacatcc agaaggagtc aactctccat ctcgtgctcc    1140
gtctccgtgg tggtggatcc atggacctgc atctaatttt cggtccaact tgcacaggaa    1200
agacgacgac cgcgatagct cttgcccagc agacagggct tccagtcctt tcgcttgatc    1260
gggtccaatg ctgtcctcaa ctatcaaccg gaagcggacg accaacagtg gaagaactga    1320
aaggaacgac gcgtctctac cttgatgatc ggcctctggt ggagggtatc atcgcagcca    1380
agcaagctca tcataggctg atcgaggagg tgtataatca tgaggccaac ggcgggctta    1440
ttcttgaggg aggatccacc tcgttgctca actgcatggc gcgaaacagc tattggagtg    1500
cagattttcg ttggcatatt attcgccaca agttacccga ccaagagacc ttcatgaaag    1560
cggccaaggc cagagttaag cagatgttgc accccgctgc aggccattct attattcaag    1620
agttggttta tctttggaat gaacctcggc tgaggcccat tctgaaagag atcgatggat    1680
atcgatatgc catgttgttt gctagccaga accagatcac ggcagatatg ctattgcagc    1740
ttgacgcaaa tatggaaggt aagttgatta tgggatcgc tcaggagtat ttcatccatg    1800
cgcgccaaca ggaacagaaa ttcccccaag ttaacgcagc cgctttcgac ggattcgaag    1860
gtcatccgtt cggaatgtat taggttacgc cagccctgcg tcgcacctgt cttcatctgg    1920
ataagatgtt cgtaattgtt tttggctttg tcctgttgtg gcagggcggc aaatacttcc    1980
gacaatccat cgtgtcttca aactttatgc tggtgaacaa gtcttagtttt ccacgaaagt    2040 attatgttaa attttaaaat ttcgatgtat aatgtggcta taattgtaaa aataaactat    2100
cgtaagtgtg cgtgttatgt ataatttgtc taaatgttta atatatatca tagaacgcaa    2160
taaatattaa atatagcgct tttatgaaat ataaatacat cattacaagt tgtttatatt    2220
tcgggtggac tagttttttaa tgtttagcaa atgtccatc agttttctct ttttgtcgaa    2280
cggtaattta gagttttttt tgctatatgg attttcgttt ttgatgtatg tgacaaccct    2340
cgggattgtt gatttatttc aaaactaaga gttttttgctt attgttctcg tctatttttgg    2400 atatcaatct tagttttata tcttttctag ttctctacgt gttaaatgtt caacacacta    2460
gcaatttggc tgcagcgtat ggattatgga actatcaagt ctgtgggatc gataaatatg    2520
cttctcagga atttgagatt ttacagtctt tatgctcatt gggttgagta taatatagta    2580
aaaaaatagg aattc    2595
```

```
<210> SEQ ID NO 4
<211> LENGTH: 292
<212> TYPE: DNA
<213> ORGANISM: Saccharomyces cerevisiae

<400> SEQUENCE: 4
```

```
ttcttcgcca gaggtttggt caagtctcca atcaaggttg tcggcttgtc taccttgcca     60
gaaatttacg aaaagatgga aagggtcaa atcgttggta gatacgttgt tgacacttct    120
aaataagcga atttcttatg atttatgatt tttattatta aataagttat aaaaaaaata    180
agtgtataca aattttaaag tgactcttag gttttaaaac gaaaattctt attcttgagt    240
aactctttcc tgtaggtcag gttgctttct caggtatagc atgaggtcgc tc           292
```

```
<210> SEQ ID NO 5
<211> LENGTH: 359
<212> TYPE: DNA
<213> ORGANISM: Solanum tuberosum

<400> SEQUENCE: 5
```

```
ttgattttaa tgtttagcaa atgtcctatc agttttctct ttttgtcgaa cggtaattta      60
gagttttttt tgctatatgg attttcgttt ttgatgtatg tgacaaccct cgggattgtt     120
gatttatttc aaaactaaga gttttgtctt attgttctcg tctatttgg atatcaatct      180 tagttttata tcttttctag ttctctacgt gttaaatgtt caacacacta gcaatttggc     240
tgcagcgtat ggattatgga actatcaagt ctgtgggatc gataaatatg cttctcagga    300
atttgagatt ttacagtctt tatgctcatt gggttgagta atatatagta aaaaaatag     359
```

```
<210> SEQ ID NO 6
<211> LENGTH: 626
<212> TYPE: DNA
<213> ORGANISM: Oryza sp.

<400> SEQUENCE: 6
agtattttcg catgaatgtt cttttcttct gtcttgtgca tcagtgatct agtgcatggg     60
agtttgtatt gtgatgttcg acatcacgta acttccactt tgcctttgct gttcgatatt    120
ttaatgacat gtcacacaca cttctgatac ttttctttct tggctattgt gccagcatga    180
tgcaagatgc atcacagcat cagatatatt ctcatcgtca ggctttagca gcacgagc     240 acgctttgcc gcttaaaagt tgtacggcgc agcttagaca tcccctgtag aagtgataat    300
cttttcactt ttccttaaac aaattgagag gggaaatgga accatgtgga tcagagaagc   360
ttttgtttct ttacacaaga atatttggta cagtgggggt cctatgttcg tgggttcgtg    420
gcttggctgc ctgtcttcaa ccaagtgttt tcagttcaac atgttagcgt gtagaaagag   480
cacaattctg tttatctcca aggtaaaatg tggcattctg ttaaagaaca tgatcctgcc    540
aattttttaa gttcaatgg aagaggaatg taaagctttc tatggtttgt gtacacaaca    600
cagtggaaga ggagtgcaag cttct                                           626
```

```
<210> SEQ ID NO 7
<211> LENGTH: 492
<212> TYPE: DNA
<213> ORGANISM: Solanum tuberosum

<400> SEQUENCE: 7
aaataacaaa tatcaatatg aggtcaataa caatatcaaa ataatatgaa aaaagagcaa    60
tacataatat aagaaagaag atttaagtgc gattatcaag gtagtattat atcctaatt    120 gctaatattt aaactcttat atttaaggtc atgttcatga taaacttgaa atgcgctata   180
ttagagcata tattaaaata aaaaaatacc taaaataaaa ttaagttatt tttagtatat   240
atttttttac atgacctaca ttttttctggg tttttctaaa ggagcgtgta agtgtcgacc   300
tcattctcct aattttcccc accacataaa aattaaaag gaaaggtagc ttttgcgtgt    360
tgttttggta cactacacct cattattaca cgtgtcctca taaattggt taaccctatg    420 aggcggtttc gtctagagtc ggccatgcca tctataaaat gaagctttct gcacctcatt   480
tttttcatct tc                                                         492
```

```
<210> SEQ ID NO 8
<211> LENGTH: 1026
<212> TYPE: DNA
<213> ORGANISM: Solanum tuberosum

<400> SEQUENCE: 8
taatatttac attagttttg ttgatgagga tgacaagatt ttggtcatca attacatata    60
cccaaattga atagtaagca acttaatgtt tttcataatg ataatgacag acacaaaaaa   120
```

```
aacccattta ttattcacat tgattgagtt ttatatgcaa tatagtaata ataataatat      180
ttcttataaa gcaagaggtc aatttttttt taattatacc aacgtcacta aattatattt      240
gataatgtaa aacaattcaa ttttacttaa atatcatgaa ataaactatt tttataacca      300
aattactaaa ttttccaat aaaaaaagt cattaagaag acataaaata aatttgagta        360
aaaagagtga agtcgactga cttttttttt tttatcata agaaaataaa ttattaactt       420
taacctaata aaacactaat ataatttcat ggaatctaat acttacctct tagaaataag      480
aaaaagtgtt tctaatagac cctcaattta cattaaatat tttcaatcaa atttaaataa      540
caaatatcaa tatgaggtca ataacaatat caaaataata tgaaaaaaga gcaatacata      600
atataagaaa gaagatttaa gtgcgattat caaggtagta ttatatccta atttgctaat     660
atttaaactc ttatatttaa ggtcatgttc atgataaact tgaaatgcgc tatattagag      720
catatattaa aataaaaaaa tacctaaaat aaaattaagt tattttttagt atatattttt    780 ttacatgacc tacatttttc tgggttttc taaaggagcg tgtaagtgtc gacctcattc       840
tcctaatttt ccccaccaca taaaaattaa aaaggaaagg tagcttttgc gtgttgtttt     900
ggtacactac acctcattat tacacgtgtc ctcatataat tggttaaccc tatgaggcgg     960
tttcgtctag agtcggccat gccatctata aaatgaagct ttctgcacct cattttttc     1020 atcttc                                                                1026

<210> SEQ ID NO 9
<211> LENGTH: 253
<212> TYPE: DNA
<213> ORGANISM: Unknown Organism
<220> FEATURE:
<223> OTHER INFORMATION: Description of Unknown Organism: Plant-like
      promoter

<400> SEQUENCE: 9
gtcgacaagc aaagggtatg gcaactgtgt caccgccctt cgctgcgtgt taacggccac       60
caaccgcagg tagcaaacgg cgtgcacctt cccgagatct ccacagcgag gtctggcttt     120
ttccgccttc ccggaaaccg cggtggtttc agcgtggcgg attccccctc ccaccaccca     180
accgccataa ataccagccc ccacctcact ctctttgcat atccatccaa atcccagtcc     240
ccaatcgaat tcc                                                        253

<210> SEQ ID NO 10
<211> LENGTH: 300
<212> TYPE: DNA
<213> ORGANISM: Zea mays

<400> SEQUENCE: 10
aagcttaata gcttcaccta tataatactt catccatttt attagtacat ccatttaggg       60
tttagggtta atggttttta tagactaatt tttttagtac atctatttta ttctatttta     120
gcctctaaat taagaaaact aaaactctat tttagttttt ttatttaata atttagatat     180
aaaatagaat aaaataaagt gactaaaaat taaacaaata ccctttaaga aattaaaaaa     240
actaaggaaa cattttttctt gtttcgagta gataatgcca gcctgttaaa cgccgtcgac     300

<210> SEQ ID NO 11
<211> LENGTH: 1425
<212> TYPE: DNA
<213> ORGANISM: Saccharum officinarum

<400> SEQUENCE: 11
```

```
gaattccctt cgtcggagaa attcatcgaa gcgaagcgaa tcctcgcgat cctctcaagg      60
tactgcgagt tttcgatccc cctctcgacc cctcgtatgt ttgtgtttgt cgtacgtttg     120
attaggtatg ctttccctgt ttgtgttcgt cgtagcgttt gattaggtat gctttccctg     180
ttcgtgttca tcgtagtgtt tgattaggtc gtgtgaggcg atggcctgct cgcgtccttc     240
gatctgtagt cgatttgcgg gtcgtggtgt agatctgcgg gctgtgatga agttatttgg     300
tgtgatctgc tcgcctgatt ctgcgggttg gctcgagtag atatgatgg ttggaccggt      360 tggttcgttt accgcgctag ggttgggctg ggatgatgtt gcatgcgccg ttgcgcgtga     420
tcccgcagca ggacttgcgt ttgattgcca gatctcgtta cgattatgtg atttggtttg     480
gacttattag atctgtagct tctgcttatg ttgccagatg cgcctactgc tccatatgcc     540
tgatgataat ccataaatgg cagtggaaat caactagttg attgcggagt catgtatcag     600
ctacaggtgt agggactagc tacaggtgta gggactgcgt ctaattgttt ggtccttaac     660
tcatgtgcaa ttatgcaatt tagtttagat gtttgttcca atcatctagg ctgtaaaagg     720
gacactggtt agattgctgt ttaatctttt tagtagatta tattatattg gtaacttatt     780
aaccctatta catgccataa cgtggattct gctcatgcct gatgataatc atagatcact     840
gtggaattaa ttagttgatt gttgaatcat gtttcatgta cataccacgg cacaattgct     900
tagttcctta acaaatgcaa attttactga tccatgtatg atttgcgtgg ttctctaatg     960
tgaaatacta tagctacttg ttagtaagaa tcaggttcgt atgcttaatg ctgtatgtgc    1020
cttctgctca tgcctgatga taatcatata tcactggaat taattagttg atcgtttaat    1080
catatatcaa gtacatacca tggcacaatt tttagtcact taacccatgc agattgaact    1140
ggtccctgca tgttttgcta aattgttcta ttctgattag accatatatc aggtattttt    1200
ttttggtaat ggttctctta ttttaaatgc tatatagttc tggtacttgt tagaaagatc    1260
tggttcatag tttagttgcc tatccttcga attaggatgc tgagcagctg atcctatagc    1320
tttgtttcat gtatcaattc ttttgtgttc aacagtcagt ttttgttaga ttcattgtaa    1380
cttatgttcg cttactcttc tggtcctcaa tgcttgcagg gatcc                    1425
```

<210> SEQ ID NO 12
<211> LENGTH: 25
<212> TYPE: DNA
<213> ORGANISM: Agrobacterium sp.

<400> SEQUENCE: 12

```
tgacaggata tattggcggg taaac                                            25
```

<210> SEQ ID NO 13
<211> LENGTH: 25
<212> TYPE: DNA
<213> ORGANISM: Agrobacterium sp.

<400> SEQUENCE: 13

```
tggcaggata tattgtggtg taaac                                            25
```

<210> SEQ ID NO 14
<211> LENGTH: 25
<212> TYPE: DNA
<213> ORGANISM: Agrobacterium sp.

<400> SEQUENCE: 14

```
tggcaggata tatccgttg taatt                                             25
```

<210> SEQ ID NO 15

-continued

```
<211> LENGTH: 25
<212> TYPE: DNA
<213> ORGANISM: Agrobacterium sp.

<400> SEQUENCE: 15
cggcaggata tattcaattg taatt                                              25

<210> SEQ ID NO 16
<211> LENGTH: 25
<212> TYPE: DNA
<213> ORGANISM: Agrobacterium sp.

<400> SEQUENCE: 16
tggtaggata tataccgttg taatt                                              25

<210> SEQ ID NO 17
<211> LENGTH: 25
<212> TYPE: DNA
<213> ORGANISM: Agrobacterium sp.

<400> SEQUENCE: 17
tggcaggata tatggtactg taatt                                              25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Consensus
      sequence
<220> FEATURE:
<221> NAME/KEY: modified_base
<222> LOCATION: (16)
<223> OTHER INFORMATION: a, t, c or g

<400> SEQUENCE: 18
ygryaggata tatwsnvbkg taawy                                              25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
tgacaggata tatggtaatg taaac                                              25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 20
tggcaggata tataccgatg taaac                                              25

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 21
tctagatgtc acagtacgga tttgtaag                                           28
```

```
<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 22
ggtcacctca ctgcccatca gggtgccggc ttc                              33

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 23
ccaacggatg gactgccgtt ccagtc                                      26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 24
catggagtga ttgtaggttt cgggac                                      26

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 25
gtccaacttg cacaggaaag ac                                          22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 26
catggatgaa atactcctga gc                                          22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 27
cacgctaagt gccggccgtc cgag                                        24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Primer
```

<400> SEQUENCE: 28
tcctaatcga cggcgcaccg gctg                                          24

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 29
ggatcctcgt catttacttt tatcttaatg agc                                33

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 30
aagcttaata gcttcaccta tataata                                       27

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 31
gtcgacggcg tttaacaggc t                                             21

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 32
gaattccctt cgtcggagaa attcatcgaa g                                  31

<210> SEQ ID NO 33
<211> LENGTH: 244
<212> TYPE: PRT
<213> ORGANISM: Myrothecium verrucaria

<400> SEQUENCE: 33

Met Ser Ser Ser Glu Val Lys Ala Asn Gly Trp Thr Ala Val Pro Val
 1               5                  10                  15

Ser Ala Lys Ala Ile Val Asp Ser Leu Gly Lys Leu Gly Asp Val Ser
            20                  25                  30

Ser Tyr Ser Val Glu Asp Ile Ala Phe Pro Ala Ala Asp Lys Leu Val
        35                  40                  45

Ala Glu Ala Gln Ala Phe Val Lys Ala Arg Leu Ser Pro Glu Thr Tyr
    50                  55                  60

Asn His Ser Met Arg Val Phe Tyr Trp Gly Thr Val Ile Ala Arg Arg
65                  70                  75                  80

Leu Leu Pro Glu Gln Ala Lys Asp Leu Ser Pro Ser Thr Trp Ala Leu
                85                  90                  95

Thr Cys Leu Leu His Asp Val Gly Thr Ala Glu Ala Tyr Phe Thr Ser

```
            100                 105                 110
Thr Arg Met Ser Phe Asp Ile Tyr Gly Gly Ile Lys Ala Met Glu Val
        115                 120                 125

Leu Lys Val Leu Gly Ser Ser Thr Asp Gln Ala Glu Ala Val Ala Glu
130                 135                 140

Ala Ile Ile Arg His Glu Asp Val Gly Val Asp Gly Asn Ile Thr Phe
145                 150                 155                 160

Leu Gly Gln Leu Ile Gln Leu Ala Thr Leu Tyr Asp Asn Val Gly Ala
                165                 170                 175

Tyr Asp Gly Ile Asp Asp Phe Gly Ser Trp Val Asp Asp Thr Thr Arg
            180                 185                 190

Asn Ser Ile Asn Thr Ala Phe Pro Arg His Gly Trp Cys Ser Trp Phe
        195                 200                 205

Ala Cys Thr Val Arg Lys Glu Glu Ser Asn Lys Pro Trp Cys His Thr
    210                 215                 220

Thr His Ile Pro Gln Phe Asp Lys Gln Met Glu Ala Asn Thr Leu Met
225                 230                 235                 240

Lys Pro Trp Glu

<210> SEQ ID NO 34
<211> LENGTH: 259
<212> TYPE: PRT
<213> ORGANISM: Aspergillus sp.

<400> SEQUENCE: 34

Met Cys Gln Asn Glu Val Glu Val Asn Gly Trp Thr Ser Met Pro Ala
1               5                   10                  15

Asp Ala Gly Ala Ile Phe Asp Gly Gly Pro Phe Ile Asn Val Pro Glu
            20                  25                  30

Ala Leu Ser Ile Glu Glu Ile Lys Phe Pro Val Asp Asp Pro Ile Val
        35                  40                  45

Glu Lys Thr Met Arg Tyr Ala Lys Ala Leu Pro Thr Glu Thr Phe
    50                  55                  60

Asn His Ser Met Arg Val Tyr Tyr Tyr Gly Met Gln Asp Cys Ala Ser
65                  70                  75                  80

His Gly Val Leu Ile Asn Arg Ser Gln Ala Leu Gly Met Ala Ile Thr
                85                  90                  95

Lys Gln Gln Phe Pro Lys Gln Ala Ser Ala Leu Ser Pro Ser Thr Trp
            100                 105                 110

Ala Leu Thr Cys Leu Leu His Asp Ile Gly Thr Ser Asp His Asn Leu
        115                 120                 125

Ala Ala Thr Arg Met Ser Phe Asp Ile Tyr Gly Gly Ile Lys Ala Leu
    130                 135                 140

Glu Val Leu Lys Gly Phe Gly Ala Thr Ser Asp Gln Ala Glu Ala Val
145                 150                 155                 160

Ala Glu Ala Ile Ile Arg His Gln Asp Leu Gly Val His Gly Thr Ile
                165                 170                 175

Thr Tyr Ile Gly Gln Leu Ile Gln Leu Ala Thr Ile Tyr Asp Asn Val
            180                 185                 190

Gly Ala His Pro Tyr Val Lys Asp Phe Gly Glu Leu Ile His Asp Thr
        195                 200                 205

Thr Arg Ser Gln Val His Glu Ala His Pro Pro Gly Glu Trp Arg Thr
    210                 215                 220

Phe Phe Ser Gly Val Ile Gln Lys Glu Gln Ala Ile Lys Pro Trp Cys
225                 230                 235                 240
```

His Thr Lys Lys Met Val Asn Val Leu Arg Lys Gly Ser Arg His Pro
              245                 250                 255
Asp Gly Gln

<210> SEQ ID NO 35
<211> LENGTH: 225
<212> TYPE: PRT
<213> ORGANISM: Saccharomyces cerevisiae

<400> SEQUENCE: 35

Met Ser Gln Tyr Gly Phe Val Arg Val Pro Arg Glu Val Glu Lys Ala
 1               5                  10                  15
Ile Pro Val Val Asn Ala Pro Arg Pro Arg Ala Val Val Pro Pro Pro
                 20                  25                  30
Asn Ser Glu Thr Ala Arg Leu Val Arg Glu Tyr Ala Ala Lys Glu Leu
             35                  40                  45
Thr Ala Pro Val Leu Asn His Ser Leu Arg Val Phe Gln Tyr Ser Val
 50                  55                  60
Ala Ile Ile Arg Asp Gln Phe Pro Ala Trp Asp Leu Asp Gln Glu Val
 65                  70                  75                  80
Leu Tyr Val Thr Cys Leu Leu His Asp Ile Ala Thr Thr Asp Lys Asn
                 85                  90                  95
Met Arg Ala Thr Lys Met Ser Phe Glu Tyr Tyr Gly Gly Ile Leu Ser
                100                 105                 110
Arg Glu Leu Val Phe Asn Ala Thr Gly Gly Asn Gln Asp Tyr Ala Asp
            115                 120                 125
Ala Val Thr Glu Ala Ile Ile Arg His Gln Asp Leu Thr Gly Thr Gly
130                 135                 140
Tyr Ile Thr Thr Leu Gly Leu Ile Leu Gln Ile Ala Thr Thr Leu Asp
145                 150                 155                 160
Asn Val Gly Ser Asn Thr Asp Leu Ile His Ile Asp Thr Val Ser Ala
                165                 170                 175
Ile Asn Glu Gln Phe Pro Arg Leu His Trp Leu Ser Cys Phe Ala Thr
            180                 185                 190
Val Val Asp Thr Glu Asn Ser Arg Lys Pro Trp Gly His Thr Ser Ser
            195                 200                 205
Leu Gly Asp Asp Phe Ser Lys Lys Val Ile Cys Asn Thr Phe Gly Tyr
210                 215                 220
Asn
225

<210> SEQ ID NO 36
<211> LENGTH: 274
<212> TYPE: DNA
<213> ORGANISM: Saccharum officinarum

<400> SEQUENCE: 36
aagcaaacgg tatagcaacg gtgttaacct gatctagtga tctcttgcaa tccttaacgg      60
ccacctaccg caggtagcaa acggcgtccc cctcctcgat atctccgcgg cgacctctgg     120 cttttccgc ggaattgcgc ggtggggacg gattccacaa ccgcgacgca accgcctctc     180
gccgctgggc cccacaccgc tcggtgccgt agcctcacgg gactctttct ccctcctccc     240
ccgttataaa ttggcttcat cccctccttg cctc                                 274

<210> SEQ ID NO 37
<211> LENGTH: 240

```
<212> TYPE: DNA
<213> ORGANISM: Artificial Sequence
<220> FEATURE:
<223> OTHER INFORMATION: Description of Artificial Sequence:
      Ubiquitin-like promoter sequence

<400> SEQUENCE: 37
aagcaaaggg tatggcaact gtgtcaccgc ccttcgctgc gtgttaacgg ccaccaaccg      60
caggtagcaa acggcgtgca ccttcccgag atctccacag cgaggtctgg cttttccgc     120 cttcccggaa accgcggtgg tttcagcgtg gcggattccc cctcccacca cccaaccgcc    180
ataaatacca gcccccacct cactctcttt gcatatccat ccaaatccca gtccccaatc    240

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 38
gaattcacat tatagcttta tattaccaag g                                    31

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 39
ggatccctgc aagcattgag gaccag                                          26
```